(12) United States Patent
Ben-Oren et al.

(10) Patent No.: US 7,867,171 B2
(45) Date of Patent: Jan. 11, 2011

(54) MANAGEMENT OF GASTRO-INTESTINAL DISORDERS

(75) Inventors: Ilan Ben-Oren, Jerusalem (IL); Julian Daich, Jerusalem (IL); Ephraim Carlebach, Ra'anana (IL); George Yariv, Jerusalem (IL)

(73) Assignee: Exalenz Bioscience Ltd., Modiin (IL)

( * ) Notice: Subject to any disclaimer, the term of this patent is extended or adjusted under 35 U.S.C. 154(b) by 1650 days.

(21) Appl. No.: 10/784,117

(22) Filed: Feb. 20, 2004

(65) Prior Publication Data
US 2005/0020931 A1 Jan. 27, 2005

Related U.S. Application Data

(63) Continuation of application No. PCT/IL02/00702, filed on Aug. 22, 2002.

(60) Provisional application No. 60/314,346, filed on Aug. 23, 2001, provisional application No. 60/392,514, filed on Jun. 28, 2002.

(51) Int. Cl.
*A61B 5/00* (2006.01)
(52) U.S. Cl. ............................. 600/532; 73/23.3; 422/84
(58) Field of Classification Search ........................ None
See application file for complete search history.

(56) References Cited

U.S. PATENT DOCUMENTS

| | | | |
|---|---|---|---|
| 4,548,805 A | 10/1985 | Sack et al. | |
| 4,830,010 A | 5/1989 | Marshall | |
| 5,499,135 A | 3/1996 | Heidemann et al. | |
| 5,787,885 A | 8/1998 | Lemelson | |
| 5,848,975 A | 12/1998 | Phillips | |
| 6,067,989 A | 5/2000 | Katzman | |
| 6,180,414 B1 | 1/2001 | Katzman | |
| 6,186,958 B1 | 2/2001 | Katzman et al. | |
| 6,548,043 B1 * | 4/2003 | Wagner et al. | 424/1.81 |
| 6,656,127 B1 | 12/2003 | Ben-Oren et al. | |

FOREIGN PATENT DOCUMENTS

WO    WO-99/40654 A1    8/1999

OTHER PUBLICATIONS

Stendal, C., "Practical Guide to Gastrointestinal Function Testing", Blackwell Science Ltd., Oxford, U.K., 1997, pp. 194-201.

Zighelboim, Jaime, et al., "Will a $NaH^{14}CO_3$ Capsule Method Accurately Measure Gastric Emptying?", Am. J. Gastroenterol., Mar. 1993, vol. 88, No. 3, p. 462-464.

(Continued)

*Primary Examiner*—Robert L Nasser
(74) *Attorney, Agent, or Firm*—Fennmore Craig, P.C.

(57) ABSTRACT

Methods of determining gastro-intestinal conditions by performing a succession of breath tests or others tests, particularly for determining the gastric emptying or gastric accomodation condition of a subject. Methods of performing successive gastric emptying tests with different test meals are also presented, enabling the gastric accommodation to be determined. The effects of different test means on the results is presented. Novel substrates for use in such tests are suggested, including the use of micro-encapsulation. Breath tests for the detection of bacterial overgrowth, lactose intolerance and combinations thereof are presented.

49 Claims, 12 Drawing Sheets

OTHER PUBLICATIONS

Horowitz, M., et al., "Gastric emptying in diabetes: clinical significance and treatment", Diabet. Med., Mar. 2002, vol. 19, No. 3, pp. 177-194.

Maes, Bart D., et al., "Gastric Emptying Rate of Solids in Patients with Nonulcer Dyspepsia", Digestive Diseases and Sciences, Jun. 1997, vol. 42, No. 6, pp. 1158-1162.

Preston, Tom, "C-Breath Test Modeling", Department of child health and school of veterinary science, University of Glasgow, 1998.

Kano, Fumiyoshi, et al., "High-Speed Intensity Modulation of 1.5 UM DBR Lasers with Wavelength Tuning", IEEE Journal of Quantum Electronics, IEEE Inc., Aug. 1990, vol. 26, No. 8, pp. 1340-1346.

Sarlet, G., et al., "Novel Mode Stabilization Scheme for Widely Tunable Lasers", 25th European Conference on Optical Communication, Nice, France, Sep. 27-30, 1999.

Gambini, P., et al., "An Accurate Technique for the Characterization of Wavelength Termal Transients in Tunable DBR Laser", Proceedings of the European Conference on Optical Communication (ECOC) Montreux, Sep. 12-16, 1993, pp. 245-248.

Mossi, Sandro, et al., "Gastric Emptying of Liquid Meals Measured Noninvasively in Humans with [$^{13}$C]Acetate Breath Test", Digestive Diseases and Sciences, Dec. 1994, vol. 39, No. 12, pp. 107S-109S.

Camilleri, Michael, et al., "Measurement of Gastrointestinal Motility in the GI Laboratory", Gastroenterology, 1998, vol. 115, pp. 747-762.

Tack, Jan, et al., "Role of Impaired Gastric Accommodation to a Meal in Functional Dyspepsia", Gastroenterology, 1998, vol. 115, pp. 1346-1352.

* cited by examiner

Fig. 7

| SUBJECT STATUS | TWO MEAL PROCEDURE | | | | | | TWO TEST PROCEDURE | | | | | |
|---|---|---|---|---|---|---|---|---|---|---|---|---|
| | $t_{1/2}$ | | | $t_{lag}$ | | | $t_{1/2}$ | | | $t_{lag}$ | | |
| | First (min) | Second (min) | Deviation (%) | First (min) | Second (min) | Deviation (%) | First (min) | Second (min) | Deviation (%) | First (min) | Second (min) | Deviation (%) |
| Asymptomatic | 107.2 | 97.2 | 9.35 | 69.2 | 52.6 | 234 | 100.8 | 91.4 | -10.3 | 44.6 | 46.6 | 4.2 |
| Symptomatic | 154.1 | 99.5 | 35.4 | 95.1 | 56.4 | 40.7 | 155.5 | 99.3 | 36.1 | 87.3 | 55.7 | 36.2 |
| Symptomatic | 173.9 | 111.8 | 35.7 | 90.1 | 52.2 | 42.0 | 204.6 | 120.6 | 41 | 112 | 76.1 | 31.8 |
| Symptomatic | 128.3 | 91.4 | 28.8 | 68.4 | 45.8 | 33.8 | | | | | | |
| Asymptomatic | 89.3 | 92.3 | -3.3 | 55.1 | 41.6 | 24.5 | | | | | | |
| Asymptomatic | 102.2 | 113.6 | -11.1 | 65.8 | 57.2 | 13.1 | | | | | | |

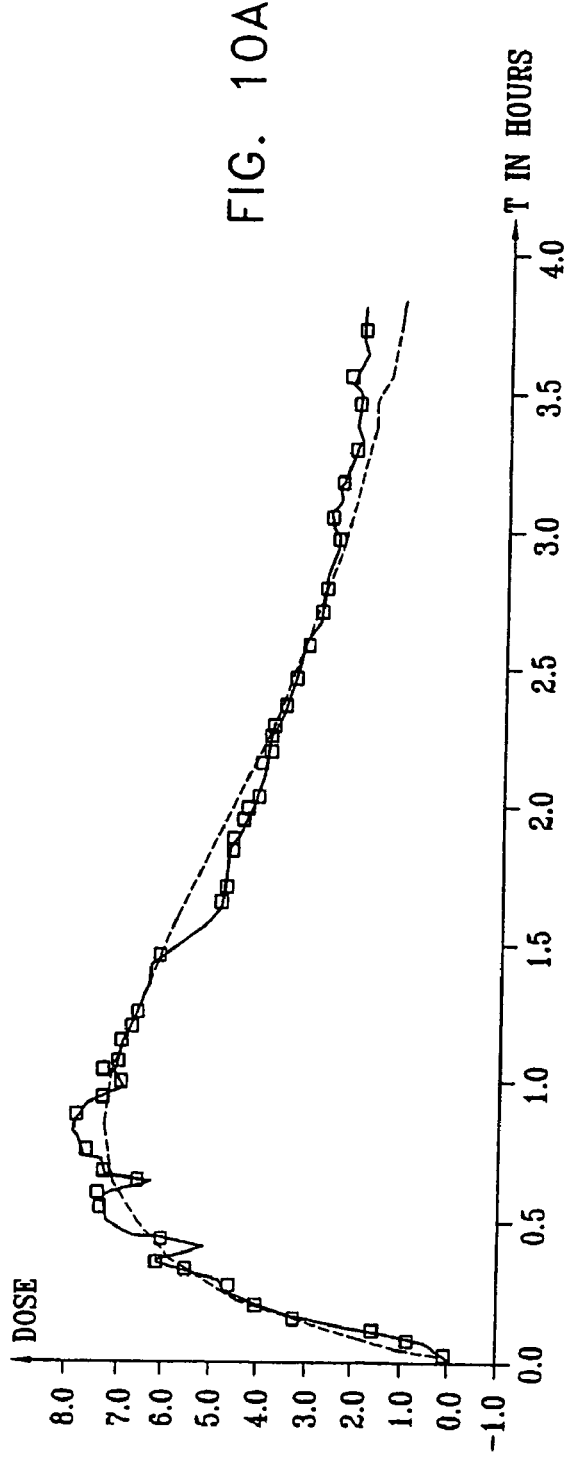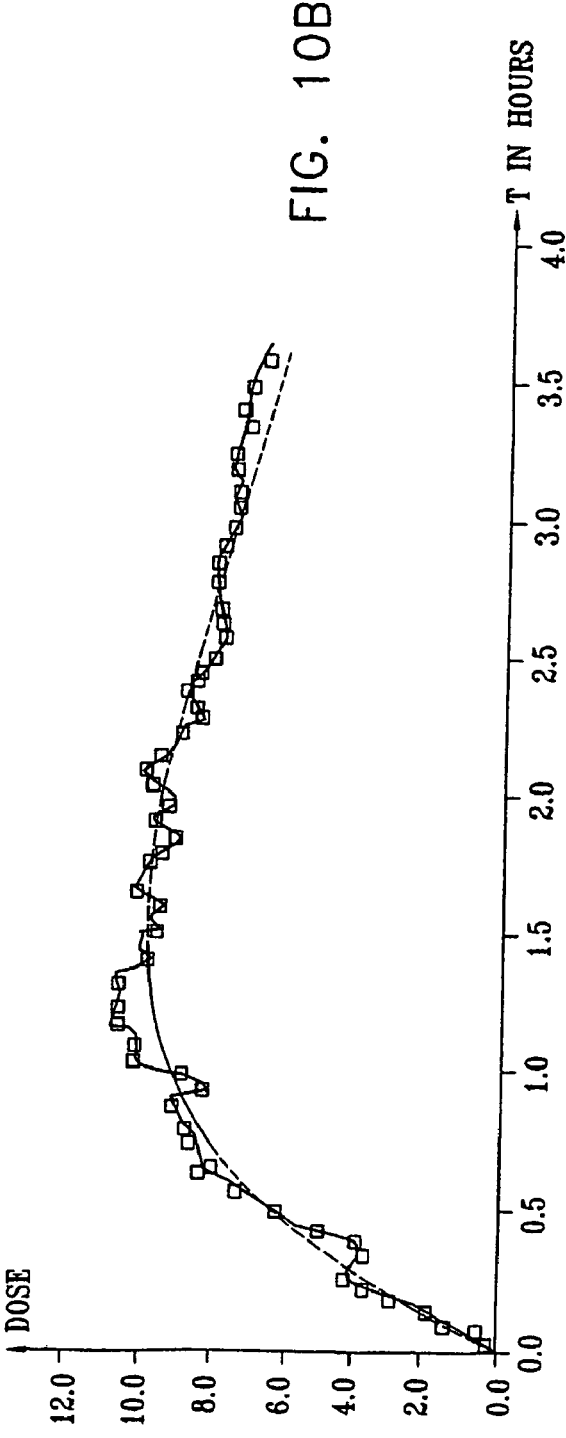

MANAGEMENT OF GASTRO-INTESTINAL DISORDERS

FIELD OF THE INVENTION

The present invention relates to the field of methods for the determination of various conditions of gastric and gastro-intestinal malfunction, especially those performed by means of breath tests.

BACKGROUND OF THE INVENTION

It is estimated that more than 25% of the general population in developed countries suffer from different degrees of functional dyspepsia and/or Irritable Bowel Syndrome, IBS. Such conditions are called for the purposes of this application, functional GI disorders. These disorders are clinical syndromes characterized by GI symptoms without identifiable cause. When a physiological cause is identified, these disorders are more correctly called organic dyspepsia or bowel disorders. The complex of dyspeptic symptoms is usually related to pain or discomfort generally felt in the center of the abdomen around or above the navel. Some examples of discomfort include fullness, early satiety, which is a feeling of fullness soon after starting to eat, bloating and nausea. There is no single organic disorder that explains all these symptoms, although about a third of all patients with these symptoms have delayed gastric emptying, though not usually so severe that it causes frequent vomiting. Additionally, a third also show a failure of the relaxation of the upper stomach following an ingestion of food, a condition known as abnormal gastric accommodation reflex. The prevalence of delayed gastric emptying in these patients is not significantly higher compared to asymptomatic individuals, but about half of the patients with these symptoms also have a sensitive or irritable stomach which causes sensations of discomfort when the stomach contains even small volumes. A gastric emptying study can show whether there is poor emptying of the stomach. Other motility disorders are more difficult to detect, but recently, there has been developed, as described for instance in "Practical Guide to Gastrointestinal Function Testing", by C. Stendal, pages 194-201, published by Blackwell Science Ltd, Oxford, U.K., (1997), methods using an intragastric balloon connected to a computer-controlled pump called a barostat, which can show:

(a) distention or whether the upper stomach relaxes adequately during eating, and
(b) how much filling of the stomach it takes to cause pain or discomfort or gastric accommodation.

Barostat studies have shown the relation between dyspepsia symptoms and impaired accommodation by means of measuring stomach volumes as a function of intra-gastric pressure, or vice versa, and/or the symptomatic response to changes in intragastric pressure at different gastric volumes. In such barostat procedures, a liquid meal is administered, which can be either a high volume of water (up to 2 liters), an isotonic or high caloric value solution such as Ensure or Gatorade, a soup or a glucagon infusion. Then, for a given volume of the balloon, the pressure needed to induce gastric discomfort or pain is measured. This method is invasive, uncomfortable to the patient and impractical for wide clinical use. Furthermore, the barostat bag may interfere with gastric motility resulting in an inaccurate result. Another example of an organic cause of dyspepsia is a *Helicobacter pylori* infection.

Asymptomatic patients in risk groups such as diabetic patients, patients under drug therapy for Parkinson's Disease, and others, also benefit from investigations for determining specific GI disorders, which can affect the prognosis of their main diseases. For example, disturbed gastric emptying may affect the glycemic control in diabetic patients.

The stomach is generally described as being divided into two separate autonomic parts-the upper, proximal or fundus, and the lower, distal or antrum. The upper (proximal/fundus) stomach distends on the entry of food, as well as acting as a food reservoir and as a pump that pushes the liquids and gastric contents out of the stomach. The function of the lower (distal/antrum) stomach is to grind food down to smaller particles and mix it with digestive juices so that it can be absorbed when it reaches the small intestine. The stomach also empties its contents into the intestine at a controlled rate to avoid excessive delivery of food or acids, which could damage or overload the small intestine.

Three types of movements can generally be discerned in the stomach:
1. Rhythmic, synchronized contractions in the lower part of the stomach, at a rate of. approximately 3 per minute, which create waves of food particles and juice which splash against the closed sphincter muscle (the pyloric sphincter) to grind the food down into small particles.
2. The upper part of the stomach shows slow relaxations lasting a minute or more that follow each swallow and that allow the food to enter the stomach maintaining constant pressure while volume is changing; at other times the upper part of the stomach shows slow contractions creating a gradient in pressure, which help to empty the stomach.
3. Between meals, after all the digestible food has left the stomach, there are occasional bursts of very strong, synchronized contractions that are accompanied by opening of the pyloric sphincter muscle. These are sometimes called "house-keeper waves" because their function is to sweep any indigestible particles out of the stomach. Another name for them is the migrating motor complex.

As previously mentioned, the barostat method is invasive, uncomfortable, impractical for wide clinical use, and may not necessarily provide accurate results. Furthermore, it is limited to determination of distension and filling disorders of the stomach alone, and other tests need to be applied for other disorders manifesting themselves in the GI tract, such as those generically related to transit time or malabsorption, or those called IBS disorders. The widespread prevalence of such gastric and GI malfunction makes it important to have a simple, quick, easily tolerable and reliable test for diagnosing and discriminating between various forms of such disorders.

The above-referenced book by C. Stendal is particularly useful as a review of the background of the subject matter of this application. The disclosures of each of the publications mentioned in this section and in other sections of the specification, are hereby incorporated by reference, each in its entirety.

SUMMARY OF THE INVENTION

The present invention seeks to provide new methods that allow a more exact diagnosis of gastric disorders in patients that suffer from dyspepsia or IBS, as well as in asymptomatic patients that are in risk groups. In particular, methods are proposed that allow a more exact diagnosis by means of dedicated breath tests for GI disorder determination. The methods, being breath tests, are also easily tolerated by the patient, and sufficiently simple that they can be performed by medical technicians, in contrast to many of the prior art tests, which could be performed only by medical doctors. Automated breath test procedures which provide real time results, such as those described in U.S. Pat. No. 6,186,958 for "Breath Test Analyzer", assigned to the assignee of the present invention, not only make the tests quicker, but also are almost essential for enabling the practical execution of some of the methods of the present invention. In addition, the preferred methods of the present invention allow control management of the treatment of such patients. The significant clinical advantage of these methods is clear, due to recent research work that show that GI patients often have symptoms which are not stable; therefore treatment according to symptoms only, without ongoing testing, may be problematic.

The disorders that can be diagnosed and followed by the preferred methods of the present invention can be divided into two groups:

(A) Dyspepsia-type disorders, generally related to feelings in the region of the stomach, including (i) delayed gastric emptying; (ii) disturbed gastric accommodation; (iii) the effects of *Helicobacter pylon* infection; and (iv) gastric chemical sensation.
(B) Irritable Bowel Syndrome type disorders, including: (v) bacterial overgrowth; (vi) Lactose intolerance; and (vii) Orocecal transit time disorders.

The assessing of different physiological findings for dyspepsia, allows the prescription of the appropriate therapy. For example, a patient with delayed gastric emptying and normal gastric accommodation can be treated with pro-kinetic therapy (including pharmacological agents, diet). In another example, a patient with abnormal gastric accommodation and a positive urea breath test for *H. pylon*, can be treated for *H. pylori* eradication alone or in combination with a fundus-relaxing drug.

There is thus provided in accordance with a preferred embodiment of the present invention, a method of determining at least one gastro-intestinal condition in a subject, comprising the steps of:
(a) performing on the subject a first breath test selected from a group of breath tests, each breath test of the group providing gastro-intestinal information related to the subject,
(b) performing on the subject at least a second breath test selected from the group of breath tests, according to the outcome of at least the first breath test, and
(c) determining from the outcome of at least one of the breath tests a gastro-intestinal condition of the subject.

In this method, the condition preferably comprises at least one of dyspepsia and irritable bowel syndrome, the dyspepsia possibly arising from at least one of a gastric emptying disorder, a gastric accommodation disorder, and a *Helicobacter pylori* infection. The irritable bowel syndrome could possibly arise from at least one of a sugar malabsorption disorder, a bacterial overgrowth, and an orececal transit time disorder. The sugar malabsorption disorder could be one or more of lactose intolerance, fructose intolerance, sucrose intolerance or maltose intolerance.

In accordance with still another preferred embodiment of the present invention, there is provided a method of providing a substrate for isotopic breath tests, comprising the step of micro-encapsulating the isotopically labeled material, wherein the properties of the micro-encapsulation coating material are chosen such that the isotopically labeled material is released in the predetermined part of the gastro-intestinal tract.

The micro-encapsulation coating material is preferably chosen such that it breaks down and releases the isotopically labeled material according to the pH value of the environment through which it is passing. According to a further embodiment, the coating material is such that it breaks down and releases the isotopically labeled material only after leaving the stomach. Furthermore, the isotopically labeled material is preferably used as a marker for determining passage of a meal through the duodenum. Alternatively and preferably, the micro-encapsulation coating material is such that it breaks down and releases the isotopically labeled material under the effect of enzymic action arising from the enzymic environment through which it is passing. The enzymes could preferably be those secreted by at least one of the pancreas and the bile ducts, such that the isotopically labeled material is used as a marker for determining passage through the duodenum.

Another preferred advantage of the micro-encapsulation coating is that it can be more readily bonded to an administered meal than the isotopically labeled material.

In accordance with yet another preferred embodiment of the present invention, there is provided method of performing a breath test for the determination of gastric emptying of a subject, comprising the steps of:
(a) providing a gas analyzer, such that breath samples can be collected from the subject or analyzed essentially continuously,
(b) collecting and analyzing the exhaled breaths of many test subjects and predetermining averaged norms for the values of at least one of the $t_{1/2}$, $t_{lag}$, delta over baseline (DoB), and Gastric Emptying Coefficient (GEC) parameters,
(c) administering to the subject a test meal comprising a labeled marker whose by-products are absorbed and exhaled in breaths of the subject after exit from the stomach of the subject,
(d) calculating in real time, as the breath test proceeds, at least one of the $t_{1/2}$, $t_{lag}$, delta over baseline (DoB), and Gastric Emptying Coefficient (GEC) parameters of the subject, and
(e) determining at the earliest possible moment, by means of extrapolation to within allowed error limits, a final estimated value of at least one of the parameters, from which it can be determined if at least one of the parameters departs significantly from the predetermined norms.

Using the above mentioned method, an indication is preferably provided of a gastric emptying disorder in the subject while the subject is still providing breath samples to the analyzer or even according to the on-going analyses of the breaths of the subject. Similarly, an indication for normal gastric emptying is provided at early stages of the test according to the value of parameters and comparison to the normal and abnormal ranges.

There is further provided in accordance with still another preferred embodiment of the present invention, a method for the determination of gastric accommodation in a subject, comprising the steps of:
(a) administering to the subject a first liquid meal comprising a first predetermined volume, preferably a small meal of the order of 200 milliliters and containing a reasonable caloric content, preferably of the order of 200 to 300 kilocalories,
(b) determining the rate of emptying of the first meal from the stomach of the subject,
(c) administering to the subject a second liquid meal comprising a second predetermined volume greater than the predetermined first volume and having a predetermined gastric retention characteristic,
(d) determining the rate of emptying of the second meal from the stomach of the subject, and
(e) determining the gastric accommodation of the subject according to the deviation between the rate of emptying of the second meal and the rate of emptying of the first meal.

According to this embodiment, the second predetermined volume is preferably sufficient to challenge gastric accommodation/relaxation in the subject, using a volume such as at least 750 milliliters of liquid.

Alternatively and preferably, the gastric retention characteristic arises from at least one of a predetermined pH, a predetermined calorific value and a predetermined composition of the liquid meal. The predetermined pH could preferably be less than 3, or the predetermined calorific value at least 200 kilocalories. The predetermined composition is preferably an isotonic composition.

In the above-mentioned method, the administering to the subject of the second liquid meal is preferably performed as soon as the rate of emptying of the first meal from the stomach of the subject is determined or is capable of being determined. Alternatively and preferably, the administering to the subject of the second liquid meal is performed after a time when essentially all physiological effects of the first meal on the subject have terminated. According to the latter criterion, the administering to the subject of the second liquid meal is performed on a successive day to the first meal.

In accordance with a further preferred embodiment of the present invention, there is also provided a method for the determination of gastric accommodation in a subject, comprising the steps of:
(a) administering to the subject a liquid meal comprising a predetermined volume and having a predetermined gastric retention characteristic, the average gastric emptying rate of the meal for a large plurality of normal subjects being known,
(b) determining the rate of emptying of the meal from the stomach of the subject, and
(c) determining the gastric accommodation of the subject according to the deviation between the rate of emptying of the meal from the stomach of the subject and the average rate of emptying of the meal for a large plurality of normal subjects.

Preferably the second predetermined volume is sufficient to cause gastric distension in the subject, such as at least 750 milliliters of liquid. Alternatively and preferably, the gastric retention characteristic may arise from at least one of a predetermined pH, a predetermined calorific value and a predetermined composition of the liquid meal. The predetermined pH is preferably less than 3, the predetermined calorific value is preferably at least 200 kilocalories, and the predetermined composition is preferably an isotonic composition.

There is also provided in accordance with yet a further preferred embodiment of the present invention, a breath test for determining the effect of the volume of a meal on the intragastric pressure, comprising the steps of:
(a) administering to the subject an isotopically labeled liquid meal comprising a predetermined volume and having a predetermined gastric retention characteristic,
(b) determining the rate of emptying of the meal from the stomach of the subject by means of a breath test performed for isotopically labeled breath, and
(c) varying the predetermined volume, and repeating the steps of administering and determining.

In any of the above mentioned methods involving rate of emptying, the determining of the rate of emptying is preferably performed by one of a breath test, scintography, an X-ray, computerized tomography, gamma imaging and an ultrasound method.

There is even further provided in accordance with a preferred embodiment of the present invention, a method for the determination of gastrointestinal disorders in a subject, comprising the steps of:
(a) administering to the subject a meal comprising at least two marker materials, a first material which is generally not absorbed in the subject's stomach, and releases hydrogen in the presence of bacteria, and a second material operative to indicate location of the meal within the gastro-intestinal tract of the subject,
(b) detecting the generation of hydrogen in the subject by means of a breath test, and
(c) determining the position within the subject's gastro-intestinal tract at which the hydrogen is generated by means of the second marker material.

In the above mentioned method, a by-product of the second marker material is also preferably detected by means of a breath test, such that the position of the hydrogen generation in the gastrointestinal tract of the subject is determined by the temporal relationship between the appearance of hydrogen and of a by-product of the marker material in the subject's breath. The second marker material is preferably labeled with a carbon isotope, and the by-product is then isotopically labeled carbon dioxide. The first material may be a sugar which in normal subjects is not metabolized in the small intestine of the subject by bacteria to generate hydrogen, such that the time of detection of hydrogen relative to the time of detection of the second marker material is used to determine the presence of bacterial overgrowth in the small intestine. The second material may be a labeled material which is metabolized in the small intestine of the subject, such that the generally concurrent appearance in the breath of the subject of hydrogen and a by-product of the second marker material is indicative of the presence of bacterial overgrowth in the subject. Alternatively and preferably, the second material is a labeled sugar also metabolized in the small intestine of the subject, such that the appearance in the breath of the subject of a by-product of the second marker material significantly prior to the appearance of hydrogen is generally indicative of the absence of bacterial overgrowth in the subject. In the above-mentioned methods, the first material is preferably at least one of glucose, lactose and lactulose.

In the above-mentioned method wherein the first material is a sugar that potentially could be metabolized in the small intestine by bacteria in said subject, such that the time of detection of hydrogen relative to the time of detection of the second marker material is used to determine the presence of bacterial overgrowth in the small intestine, this second material is preferably at least one of labeled sodium acetate, sodium octanoate, glucose, a probe such as acetyl leucine, or a microencapsulated labeled substrate In the above last mentioned methods, the first material is preferably a sugar generally that is not metabolized in the small intestine of the subject, such that detection of hydrogen essentially following detection of a small quantity of the second marker material is used to determine the orocaecal transit time of the subject.

Furthermore, in accordance with yet more preferred embodiments of the present invention, in the above described methods, the first material may be a sugar of a group thought to be malabsorbed in the small intestine of the subject, such that it arrives essentially unabsorbed at the colon of the subject, where hydrogen is generated by the presence of colonic bacteria, such that the time of detection of hydrogen relative to the time of detection of the second marker material is used to determine a sugar intolerance in the subject. A practical example is lactose intolerance.

In such a case, the second material is preferably an isotopically labeled material generally absorbed in the colon, such that detection of hydrogen essentially concurrent with detection of labeled by-products of the second marker material is used to determine a sugar intolerance in the subject. Particulary and preferably, the second material is xylose labeled with a carbon isotope, and the by-product is isotopically labeled carbon dioxide.

Additionally, the second material may be an isotopically labeled material generally absorbed in the small intestine, such that the relative time and quantity of detection of hydrogen and labeled by-products of the second marker material is used to determine whether the subject is suffering from one or both of a sugar intolerance and a bacterial overgrowth. In such a case, the detection of a small quantity of hydrogen, characteristic of a small part of the first material in the presence of bacteria, occurring essentially concurrently with the detection of the labeled by-products of the second marker material indicates that the subject is suffering a bacterial overgrowth. On the other hand, the detection of hydrogen later than the detection of the labeled by-products of the second marker material indicates that the subject is suffering from a sugar intolerance, while the detection of a large quantity of hydrogen, characteristic of the majority of the first material in the presence of bacteria, occurring essentially concurrently with the detection of the labeled by-products of the second marker material indicates that the subject is suffering a sugar intolerance and a bacterial overgrowth. In any of the above mentioned methods, the sugar is at least one of the group consisting of lactose, fructose, maltose and sucrose.

BRIEF DESCRIPTION OF THE DRAWINGS

The present invention will be understood and appreciated more fully from the following detailed description, taken in conjunction with the drawings in which:

FIG. 7 is a table showing the deviation of the gastric emptying parameters between a series of subjects, some showing abnormal gastric accommodation and some being asymptomatic for two-meal and two-test procedures;

FIGS. 10A and 10B show schematic samples of gastric emptying curves from symptomatic subjects for the second day test. In FIG. 10A, a 200 ml. high caloric test meal is administered and in FIG. 10B, an 800 ml. high caloric test meal is administered.

DETAILED DESCRIPTION OF PREFERRED EMBODIMENTS

Figure 1A:
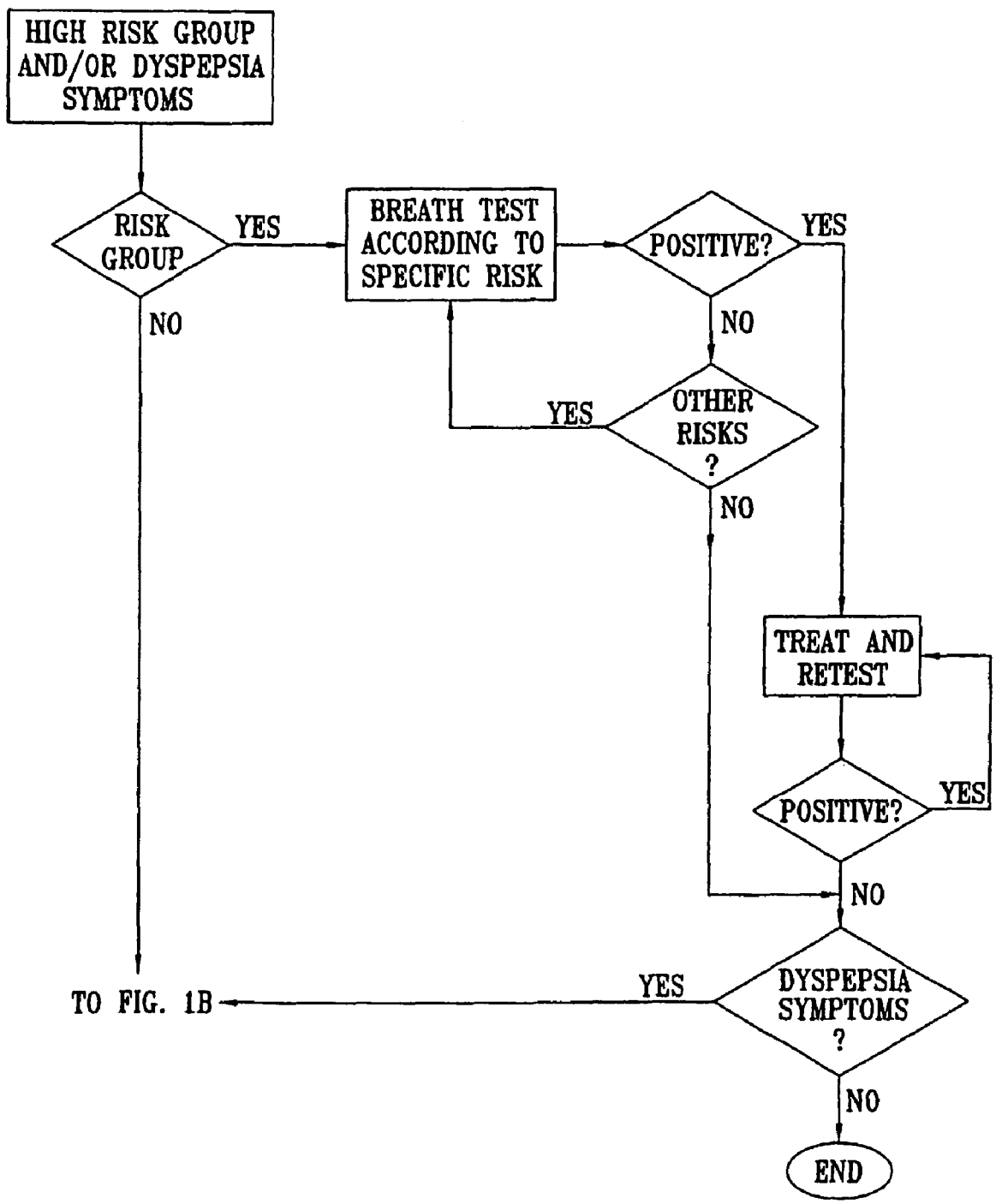
FIGS. 1A and 1B show schematic flow charts describing possible courses of detection and treatment for asymptoinatic patients belonging to a GI high risk group (FIG. 1A), or for patients with symptoms of dyspepsia or IBS (FIG. 1B)
Figure 1B:
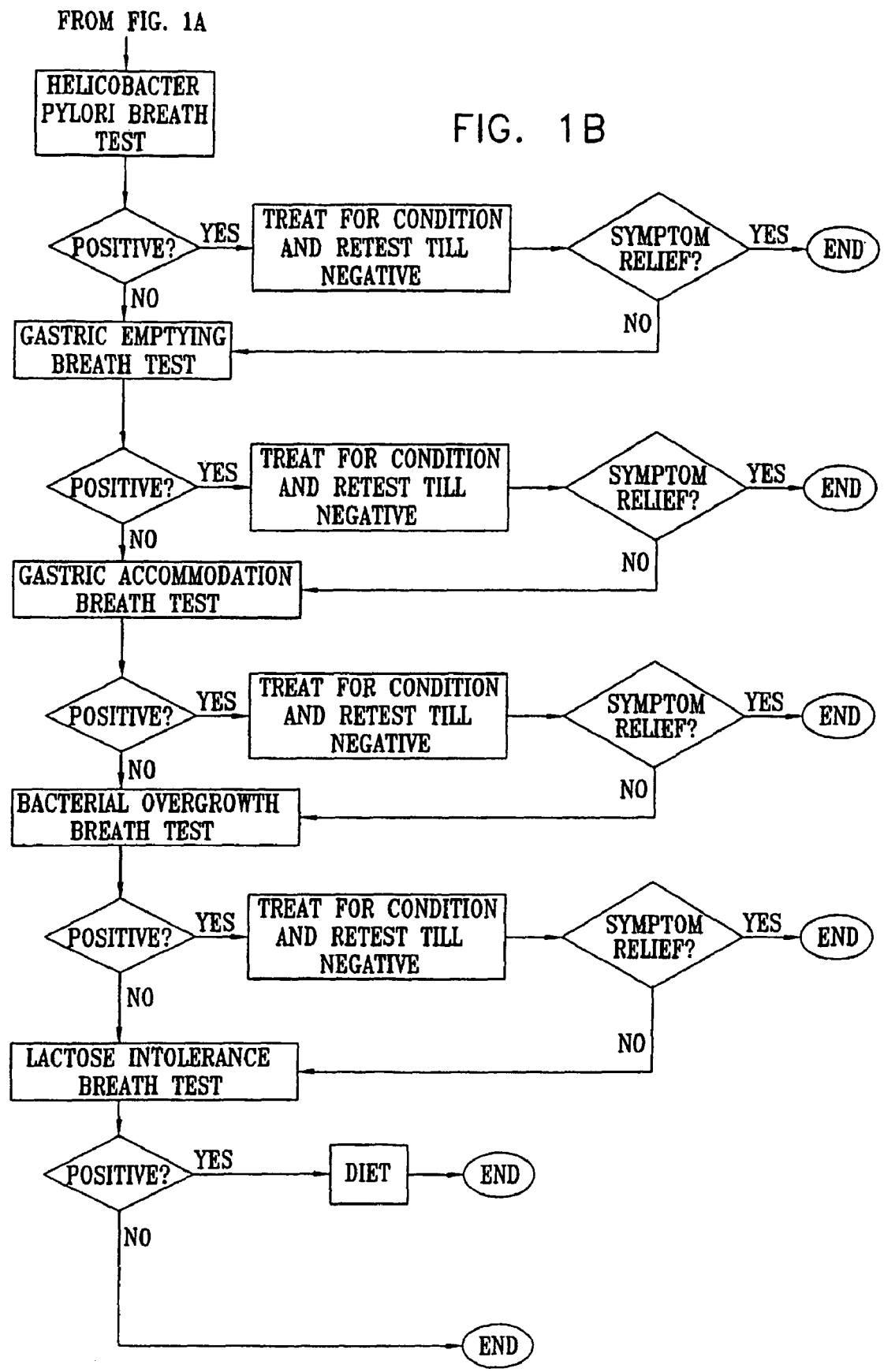

Reference is now made to FIGS. 1A and 1B, which illustrates schematically a flow chart describing possible courses of detection and treatment for patients with symptoms of dyspepsia or IBS, or asymptomatic patients belonging to a GI high risk group, as defined hereinabove. The flow chart is not intended to illustrate a definitive algorithm for a comprehensive diagnosis and treatment routine, but rather to illustrate some of the possible courses open to the treating physician, which can be taken using the methods and apparatus of the preferred embodiments of the present inventions. Though the tests in the preferred methods illustrated in FIGS. 1A and 1B are described as breath tests, it is to be understood that they can be equally well performed by other methods, as described hereinbelow.

Figure 1C:
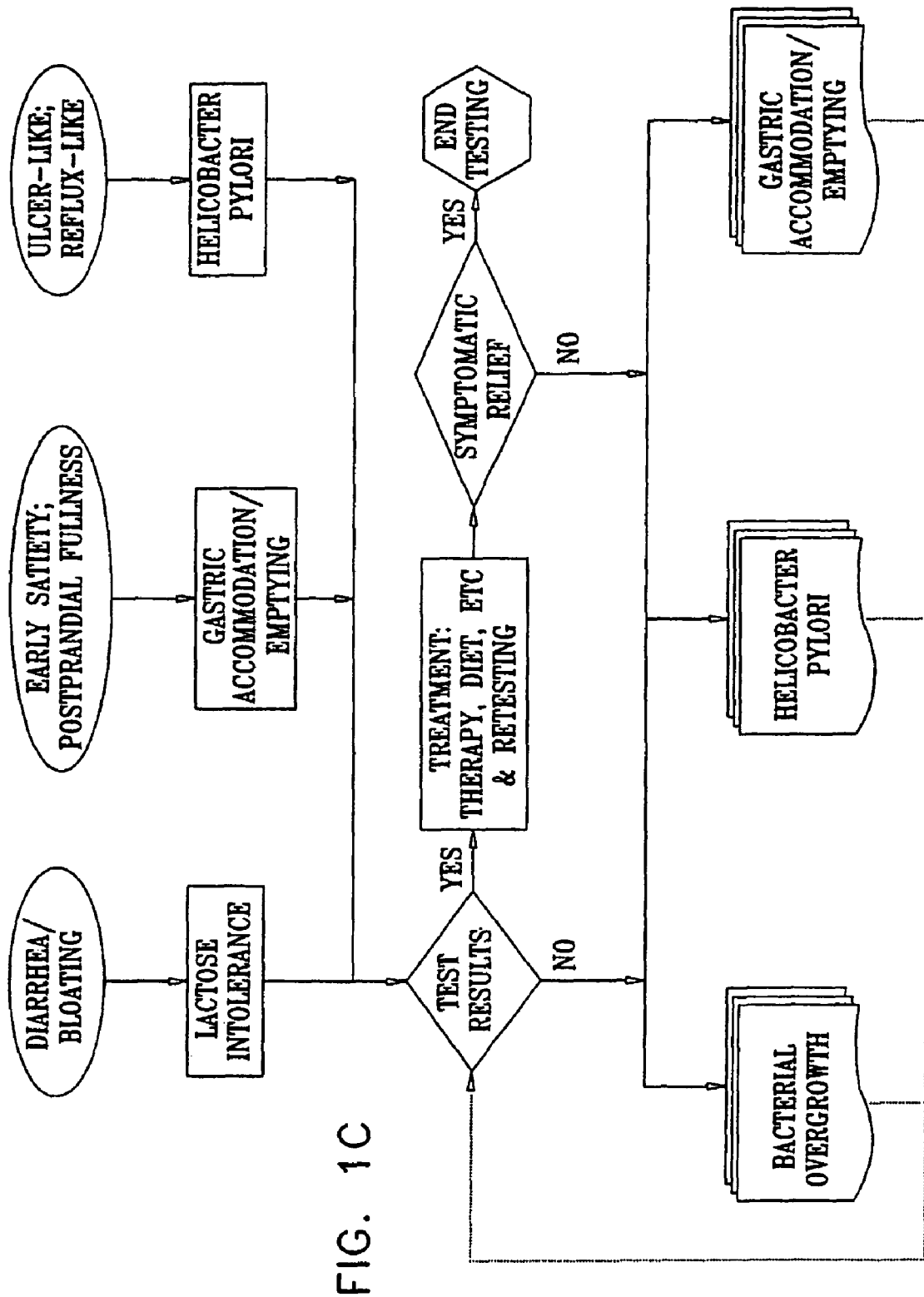
FIG. 1C is an alternative schematic diagram for illustrating a method of detection and treatment for patients suspected of having any of the above-mentioned GI problems, showing the proposed tests organized in a parallel arrangement.
Figure 2A:
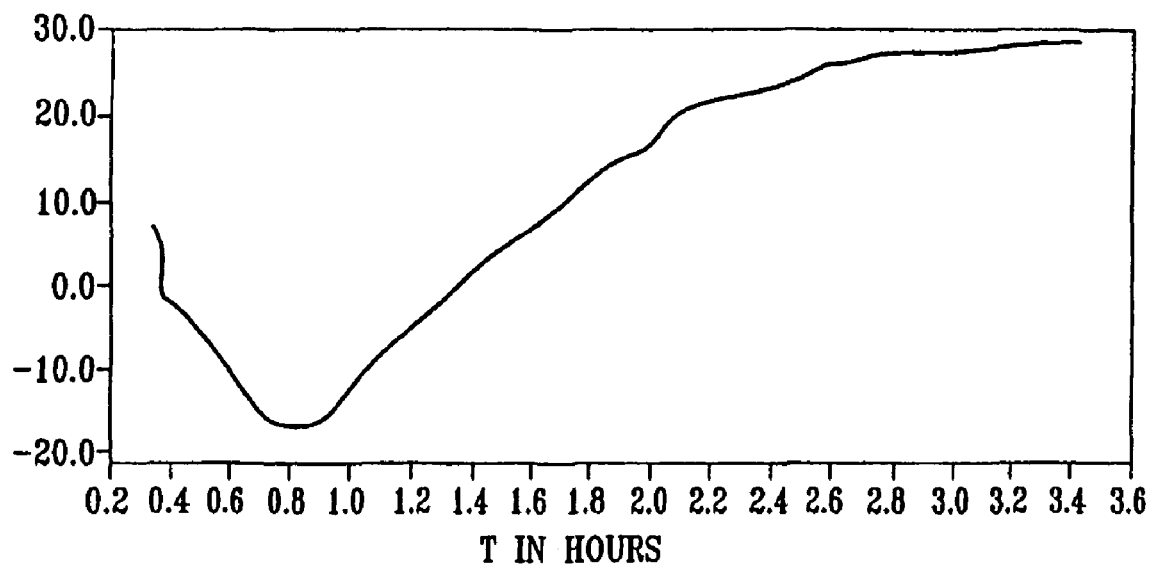
FIG. 2A to 2D are a set of four graphs showing an example of the real time progress of the calculated $t_{1/2}$, $t_{lag}$, DoB and GEC gastric emptying parameters of a subject, as a function of time in hours.
Figure 2B:
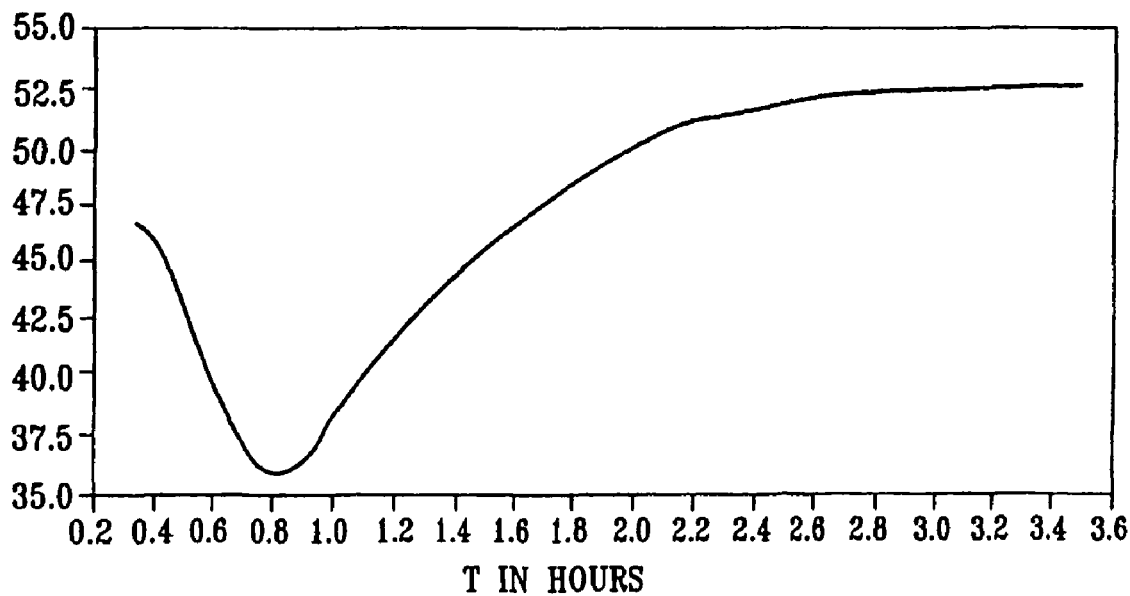
Figure 2C:
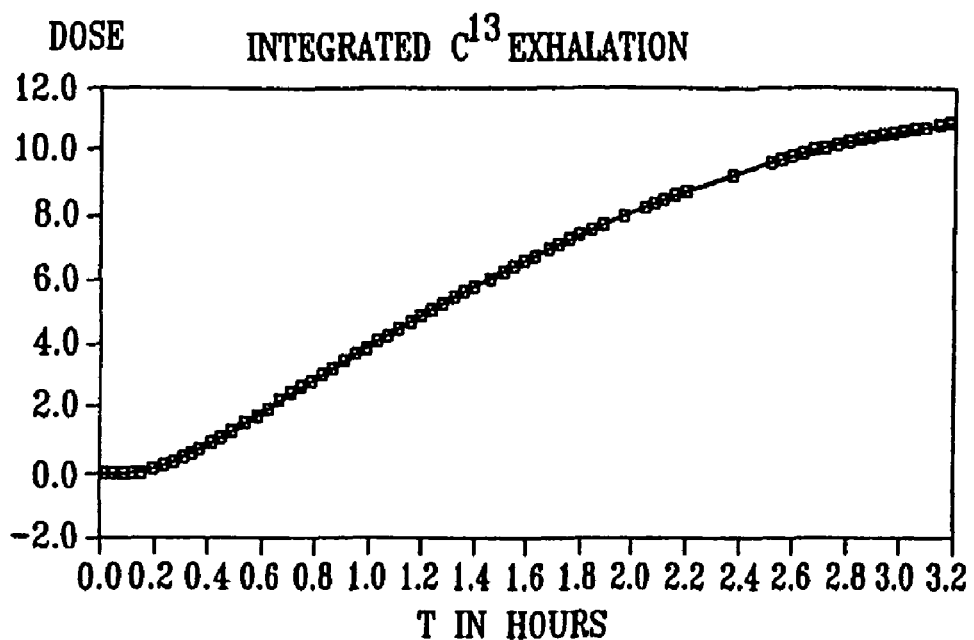
Figure 2D:
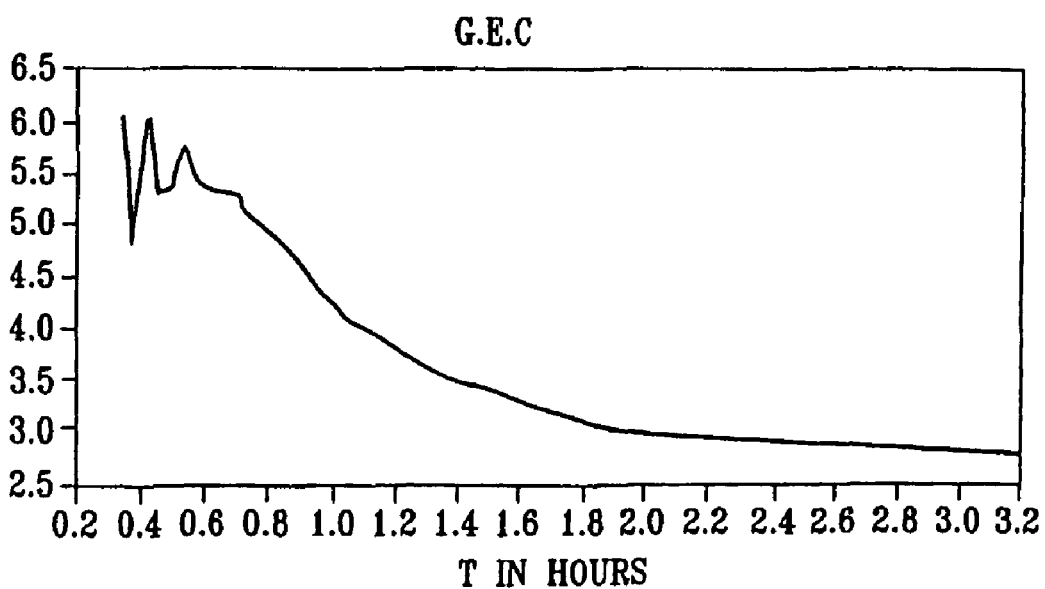

Reference is also made to FIG. 1C, which is an alternative schematic diagram for illustrating a method of detection and treatment for patients suspected of having any of the above-mentioned GI problems. In the flow chart of FIG. 1C, the proposed tests are organized in a parallel arrangement, such that the physician can perform the required tests in the order of the intensity or the urgency of the patient's symptoms. Thus, for example, a subject suffering from gastric reflux would first be tested for H-p infection, and only if the test proved negative, or if the test were positive and the treatment did not provide symptomatic relief, would it be necessary to initiate another test other than for H-P.

More detailed explanations are now presented of the methods of executing each of the breath tests shown in FIG. 1B, according to the methods of preferred embodiments of the present invention.

1. Breath Test for *Helicobacter pylori*

The breath test for *Helicobacter pylori* infection is well documented in U.S. Pat. No. 6,067,989 for "Breath Test for the Diagnosis of *Helicobacter pylorl* in the Gastrointestinal Tract", assigned to the assignee of the present application, and herein incorporated by reference in its entirety, and no further details are therefore presented here of the test itself. The use and position of the test in the diagnostic hierarchy of FIG. 1B is described above, and below in relation to FIG. 1C.

2. Gastric Emptying Breath Test (Gebt)

Symptoms related to delayed gastric emptying include nausea, vomiting and unstable glucose levels in diabetic patients. Poor emptying of the stomach can occur for several reasons:

1. The outlet to the stomach, including the pylorus and duodenum, may be obstructed by an ulcer or tumor or by a large and indigestible item that was swallowed.
2. The pyloric sphincter at the exit to the stomach may not open enough or at the right times to allow food to pass through. This sphincter is controlled by neurological reflexes to ensure that only very tiny particles leave the stomach and to limit the amount acid or food that can leave the stomach at one time to enter the small intestine. These reflexes depend on nerves which can sometime become damaged.

3. The normally rhythmic, 3-per-minute contractions of the lower part of the stomach can become disorganized so that the contents of the stomach are not pushed towards the pyloric sphincter. This also usually has a neurological origin; the most common cause is longstanding diabetes mellitus, but in many patients the cause of delayed gastric emptying is unknown, so the diagnosis is given as idiopathic gastroparesis.

Methods for the determination of gastric emptying of solids has been previously developed using radioisotopically labeled carbon substrates, in the field of scintigraphy. In such methodology, the progress in the emptying of the labeled substrate from the stomach is followed, generally by direct imaging of the radiation emitted from the radioisotope. Breath tests for measuring similar time parameters have been proposed, in which the progress in the emptying of the labeled substrate from the stomach is followed from the labeled exhaled from the subject's breath, rather than by measuring what is left in the patient's body. Prior art gastric emptying breath tests (GEBT) commonly classify patients as normal, slightly delayed and delayed, according to the test protocol used.

Prior art GEBT's are generally performed by administering, in most of the cases, a solid test meal of 150-350 kilocalories, with a substrate labeled with either $C^{13}$ or $C^{14}$ as a marker. Examples of such substrates are Octanoic Acid, Sodium Octanoate, Sodium Acetate or Acyl Amino Acid as Acetyl Leucine, and others.

The optimal characteristics of these substrates are:
1. Good bonding to the test meal in the acidic environment of the stomach;
2. Rapid release from the test meal when it leaves the stomach;
3. Immediate absorption, metabolization and conversion to measurable $CO_2$;
4. Dual usage for GEBT of liquids and solids for clinical simplicity; and
5. Easy preparation and reasonable cost.

Currently utilized substrates fulfill only some of these characteristics. Octanoic acid can be firmly bonded after cooking to the solid fats used in the meals. It is also quickly released from the food when passing through the duodenum, but after being absorbed in the small intestinal walls, it needs to be transported to the liver and metabolized there to produce $CO_2$. These processes are not directly related to the gastric emptying rate and can extend for a not insignificant time beyond the gastric emptying time, and are thus sources of delay in detecting the true gastric emptying rate. Furthermore, variability in the results may also be generated, since the $CO_2$ release is dependent on liver function, which may vary from subject to subject. Thus for example, it has been noted that even temporary impairment of liver function resulting from the consumption of a moderate quantity of alcohol can affect gastric emptying measurements for some time after the consumption, even though it would appear that that the gastric emptying rate itself is probably unaffected by the previous alcohol consumption.

In addition, octanoic acid handling requires special equipment and meal preparation is unsuited and clumsy for performing in the clinical setting. Meal preparation outside the clinical setting, on the other hand, has the disadvantage that regulatory approval is required for the whole of the meal and for its manufacturing process, and not just for the labeled substrate, as is commonly accepted in most breath tests. Therefore, such a procedure requires a high level of standardization and its associated costs are high.

Sodium octanoate is the sodium salt of octanoic acid. It is easier to handle than the octanoic acid itself, and is released from solids after leaving the stomach but it suffers from the same indirect metabolism path as octanoic acid, and is not easily mixed homogeneously with a solid meal.

Sodium acetate is considered the optimal substrate for the measurement of gastric emptying of liquids and semi-solids. This very simple and low cost substrate is rapidly metabolized after passing through the duodenum and readily converted into $CO_2$. However, it is easily diluted by water and acidic media, and in the gastric environment, is easily detached from its meal base, such that progress does not necessarily reflect the emptying rate of the meal. Therefore it is clinically unpractical for use with solid meals. Furthermore, the need to bond it to a solid meal by industrial food preparation techniques gives it some of the disadvantages of octanoic acid.

Acyl Amino Acid as Acetyl Leucine has been recently proposed as an alternative GEBT substrate, and does not suffer from most of the technical drawbacks of the octanoates related to bonding, metabolization and versatility, but it is of higher cost. Furthermore, since it is not a naturally occurring substance, it may require a complex regulatory process before approval for use.

Sodium bicarbonate has also been proposed as an alternative substrate due to its being a readily accessible and abundant source of $CO_2$, and because of its simplicity and low cost. However, it too cannot be easily bonded to food, and releases its $CO_2$ content too readily through the gastric walls, making it impractical to use.

A breath test using an encapsulated version of $^{14}C$-labeled sodium bicarbonate was attempted by Zighelboim et al, as described in the article "Will a $NaH^{14}CO_3$ capsule method accurately measure gastric emptying?", published in Am. J. Gastroenterol. Vol. 88(3), pp.462-4, Mar. 1993. The test was unsuccessful, since the capsule used was bigger than the 2mm size of the particles that the stomach evacuates as "liquid" food and was not bonded to the meal. Gamma camera measurements showed that it remained in the stomach after the food had emptied.

In performing a GEBT, one breath sample is usually taken as a baseline before administration of the meal, followed by breath samples during 4 hours usually taken every 15 min. The breath samples are analyzed by means of mass spectrometry, non dispersive infrared spectrometry, or any alternative method of isotopic analysis. The rate of metabolization of the substrate is determined from the change in $^{13}CO_2$ exhalation (delta over baseline; DoB) and the curve of the metabolized substrate excretion determined and expressed as $$y=a*t^{b}*\exp(-c*t)$$

wherein a, b and are parameters to be fitted according to the measurement curve, such as by means of a least square fit.

A cumulative curve of the substrate excretion is then computed from the integral of the last curve as $$Y_c=m*(1-\exp(-\kappa*t))\beta$$

and the parameters m, κ and β, calculated. In order to derive these parameters an estimation of the $CO_2$ rate of production is derived based on the height and weight of the subject being tested.

There are three traditional parameters, derived from a GEBT, which describe the gastric emptying outcome of a patient.

1. The half emptying time ($t_{1/2}$) or the time in which half of the test meal has left the stomach, computed by setting $yc=m/2$.
2. The lag time ($t_{lag}$) defined as the time in which the emptying of solid phase of food begins after the initial liquid phase emptying.
3. The gastric emptying coefficient (GEC) equal to log a. This parameter is related to the amplitude of the substrate recovery curve.

Preferred embodiments of the present invention relating to gastric emptying breath tests are now described. One of the advantages of the methods of the present invention is the calculation and analysis of any of the above parameters in real time while measuring and determining when there is enough data to distinguish between patients with normal, slightly delayed and significantly delayed emptying. This therefore significantly shortens the time taken to achieve a definable result, from the four hours currently needed by prior art methods, such as using mass spectrometry measurements. Another significant advantage of the preferred embodiments of the methods of the present invention is the possibility to follow changes in the dynamics of the gastric emptying, such as clearly identifying the peak or physiology noise in the emptying process. Suitable devices and methods for performing breath tests are described in the above-mentioned U.S. Pat. No. 6,186,958 for "Breath Test Analyzer"; in U.S. patent application Ser. No. 09/542,768 for "Breath test Methods and Apparatus", and in U.S. patent application Ser. No. 09/508,805 for "Isotopic Gas Analyzer", all assigned to the assignee of the present application, and all incorporated herein by reference in their entirety.

There are 3 stages in this procedure:
1. Determining normal and abnormal values, or ranges of values, of $t_{1/2}$, $t_{lag}$, Delta over baseline (DoB), and Gastric Emptying Coefficient (GEC) parameters by accumulating data from many test subjects.
2. Testing a subject and monitoring, in real time, the calculated $t_{1/2}$, $t_{lag}$, amplitude of DoB, and Gastric Emptying Coefficient (GEC), as the measurement proceeds.
3. Following the monitored graphs of these 4 parameters as they progress during the measurement, and determining by means of extrapolation at the earliest possible moment, a final estimated value, within the allowed error limits, at which it can be determined if one of the 4 parameters ($t_{1/2}$, $t_{lag}$, DoB or GEC) is abnormal, or if they are all normal. The error allowed can be a function of the estimated value obtained. When values are far from the border between the normal or abnormal ranges, larger errors can be tolerated than when borderline values are obtained.

As an example of the execution of this preferred procedure, table 1 shows the results of testing a single subject four times by administering 100mg of $^{13}$C-labeled octanoic acid and Acetyl Leucin as markers with a solid test meal of 150-350 kilocalories. The table shows the times after the peak when each of the 4 parameters were extrapolated to within 85% and 70% of their final asymptotic converged values.

TABLE 1

Estimated Time After Peak Necessary to Reach 85% & 70% Accuracy of GEBT Parameters (with extrapolation) for a Single Subject

| Test # | Time to peak (hours) | $t_{1/2}$ 85% | $t_{1/2}$ 70% | $t_{lag}$ 85% | $t_{lag}$ 70% | GEC 85% | GEC 70% | DoB Amplitude |
|---|---|---|---|---|---|---|---|---|
| 1 | 1.3 | 0.5 | 0.5 | 0.5 | 0.5 | 0.2 | 0.1 | immediate |
| 2 | 1 | 0.8 | 0.6 | 0.6 | 0.4 | 0.3 | 0.1 | immediate |
| 3 | 1 | 1 | immediate | 1 | immediate | 0.3 | 0.2 | immediate |
| 4 | 1.3 | 0.7 | 0.3 | 0.7 | immediate. | 0.1 | immediate | immediate |

There are cases of subjects with rapid gastric emptying, in whom a high DoB amplitude may be obtained even before the peak is reached, as determined by comparison with the typical time taken to reach the peak and the DoB levels reached in a normal subject.

Reference is now made to FIGS. 2A to 2D, which are a set of four graphs showing an example of the real time progress of the calculated $t_{1/2}$, $t_{lag}$, DoB and GEC of a chosen subject, as a function of time in hours. Curve fitting of the measured points was determined by applying the Levenberg-Marquat algorithm and using the Lab View program, supplied by National Instruments Corporation, of Austin, Tex. 78759, which is built into the breath analyzer, which may preferably be a model BreathID, supplied by Oridion Medical Ltd., of Jerusalem Israel. Initial guess values for the previously described coefficients a, b and c, are derived from the expected values of $t_{1/2}$, $t_{lag}$ and GEC provided by the published literature. In this example, extrapolation may be performed for the four gastric emptying parameters after approximately 1 hour.

Because there is sometimes no correlation between symptoms and delayed gastric emptying, the GEBT as described above is especially useful in the periodic management of diabetic patients for insulin/drug-food management as discussed in Gastric emptying in diabetes: clinical significance and treatment. Diabet Med. 2002 Mar;19(3):177-94. In the case of dyspepsia, dyspeptic symptoms are the main reason to test patients. It has been shown in the article by Maes BD, et al., entitled "Gastric emptying rate of solids in patients with nonulcer dyspepsia" published in Dig. Dis. Sci., Vol. 42(6), pp. 1158-62, June 1997, that delayed gastric emptying is not necessarily the origin of all dyspeptic symptoms, though first generation drugs for the treatment of gastric emptying, such as Cisparide or Erythromycin, generally help to reduce dyspeptic symptoms. The effectiveness of new emerging medicines, such as the newly proposed Tegaserod, in relieving these symptoms is not clear enough yet, but since such drugs were designed to be more GI disorder specific than those previously mentioned, diagnostic may be recommended before the drug is prescribed. This is especially important due to the fact that these drugs apparently treat the GI condition but do not cure it, and have to be administered continually to treat the disorder.

Other gastric motility disorders, related with visceral perception of pain, early fullness and bloating, include manifestations of impaired gastric distention and accommodation, for which the proper treatment includes the administration of drugs to relax the muscular tone, such as Glyceryl Trinitrate, serotonigenic agents or some antidepressants. Currently barostat studies are the only clinical method in clinical use to measure these disorders.

According to the preferred embodiments of the present invention, there is also provided a noninvasive, accurate and convenient method for the measurement of the severity of these gastrointestinal conditions related to gastric emptying and other gastric motility disorders.

In addition, according to more preferred embodiments of the present invention, there is also provided a substrate for isotopic breath tests that overcomes the disadvantages of the present available substrates. The substrate utilizes micro-encapsulated isotopically labeled material, such as is used in the food industry, and in the pharmaceutical industry for controlled drug release. The coating material can preferably be such that is broken down in the duodenum or the small intestine, rather than in the stomach, due to the higher pH in those parts of the GI tract, typically 6, compared with that in the stomach, typically 2.5 to 3.5. Alternatively and preferably, a coating broken down by specific enzymes found only in the desired part of the GI tract can be used.

These capsules are preferably filled with $^{13}C$-labeled substrate of the simplest materials, such as sodium bicarbonate or sodium acetate. Micro-encapsulation thus allows specific marker drug release of such materials along the duodenum in a rapid and homogenous way, only after emptying of the meal from the stomach.

Substrates such as octanoic acid are usually incorporated into egg yolk and an omelet is prepared therefrom as the test meal. It is know that micro encapsulation is produced during the meal cooking, since oils from the egg yolk form a hydrophobic coating around the octanoic acid and protect it during the cooking process, providing its good bonding characteristics to the meal.

As previously mentioned, according to another preferred embodiment of the present invention, micro-encapsulation can be used wherein the coating is decomposed by means of a selected enzymatic, rather than pH environment. The selectivity in this method relies on the presence of specific enzymes in the duodenum, such as those secreted by the pancreas or through the bile ducts. The advantages of this preferred embodiment are that it can be used for the micro-encapsulation for liquid meals, and also is not dependent on the variability of pH between subjects.

These preferred methods of the use of micro-encapsulated substrates have a number of advantages over prior art substrates, as follows:

1) Enablement of real time analysis of gastric emptying, since the micro-capsules are homogeneously distributed in ingested food.
2) Specific release of the substrate material, such as sodium acetate or bicarbonate, in the duodenum or small intestine or colon, in a rapid and homogeneous way, only after emptying from the stomach. The release can be made pH dependent or specific Enzyme dependent. Furthermore, the absorption of the substrate can be achieved without the need of an additional metabolic step.
3) Possibility of using the same material for both solid and liquid meals, since the bonding properties to food, the stability within the gastric environment, the taste, the convenience of use, etc., are independent of the material itself, and dependent only on the properties of the chosen micro-encapsulation coating.
4) Enablement of the use of low cost $^{13}C$ markers, while micro-encapsulation itself is a reasonably low cost process, costing in the region of tens to one hundred dollars per kilogram.

3. Breath Test for Gastric Accommodation (GABT)

An upper stomach with proper accommodation characteristics allows it to maintain constant pressure while the volume increases. This part of the stomach is responsible for gastric emptying of liquids and has almost no effect on gastric emptying of solids. The lower part of the stomach is not thought to have a significant effect on gastric emptying of liquids. In addition it is known from the literature that excess intragastric pressure is related to upper gastrointestinal symptoms and that inhibition of gastric emptying is required when high calorie meals are administered.

There is therefore provided, according to yet more preferred embodiments of the present invention, gastric accommodation breath tests (GABT) based on the principle that for different distension volumes, the gastric emptying rate of liquids is unaffected in normal individuals, but is impaired for patients with impaired accommodation.

Two methods for performing these GABT's are proposed, according to different preferred embodiments of the present invention:

A. The Two Meal Method.

Figure 4:
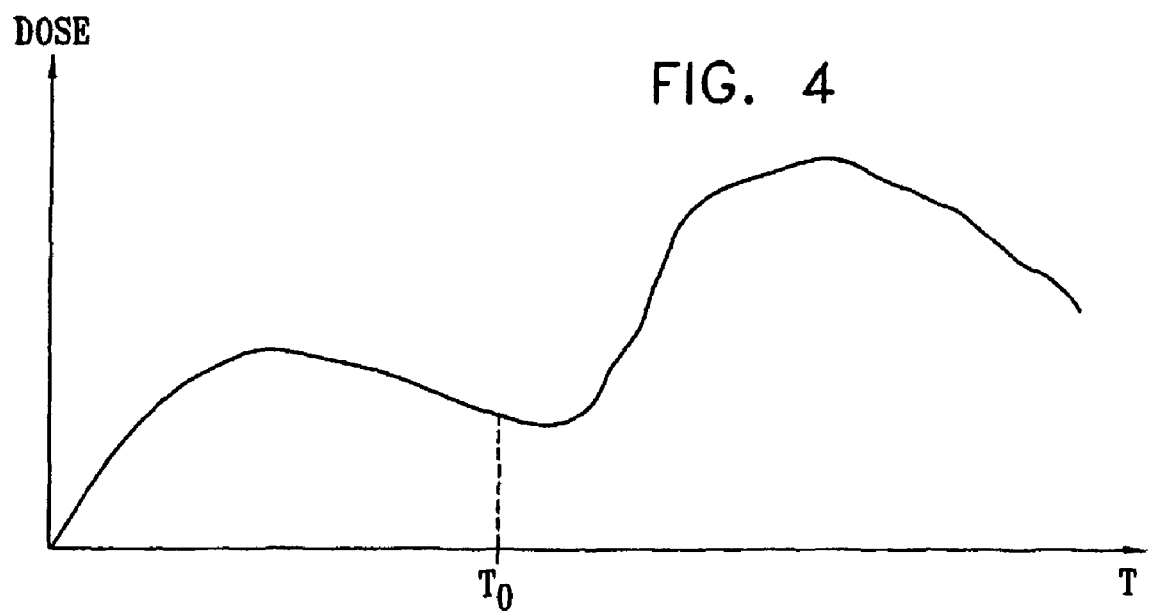
FIG. 4 is a typical DoB curve as a function of time, resulting from the two meal procedure for a subject with a normal gastric accommodation function.

A low volume, preferably of the order of 150 ml to 300 ml of a liquid meal containing a $^{13}C$-labeled substrate is administered to the subject, in a similar manner to that known in prior art gastric liquid emptying breath tests, such as described by Mossi et al., in Digestive Diseases and Sciences, Vol. 39, No. 12, December 1994 Suppl., pp. 107S-109S, incorporated herein by reference. A suitable $^{13}C$-labeled substrate may comprise, but is not limited to, sodium acetate, glucose, sodium octanoate, acetyl-leucine, Spirulina algae, micro-encapsulated bicarbonate or another substrate, preferably undergoing direct and fast metabolism, which can be utilized for the measurement of the liquid gastric emptying rate. The isotopic ratio in the exhaled breath is measured at baseline and thereafter at regular intervals in real time. A Delta over Baseline curve is preferably traced and a curve of the rate of liquid emptying or emptying from the stomach is determined from the outcome. A typical DoB curve as a function of time, resulting from this procedure is shown on the left hand part of FIG. 4, and this is the typical shape of a normal gastric accommodation curve.

According to the methods of these preferred embodiments of the present invention, a second liquid meal, preferably comprising at least one of:
1) a high volume of water, such as 1 liter;
2) an isotonic solution;
3) an acidic solution, such as one having a pH of 2.5;or
4) a caloric liquid meal;

is administered to the subject to induce gastric distention, and/or to limit the rate of gastric emptying. This second meal is administered at time $T_0$ as soon as enough data has been accumulated from the first curve to evaluate the gastric emptying rate of the first meal to the required accuracy, as described hereinabove in the section on the breath test for gastric emptying rate. $T_0$ is shown on the curve in FIG. 4, and in those figures thereafter where $T_0$ is indicated. The change in slope on the emptying curve, or the change in the gastric emptying parameters, such as $t_{1/2}$ or $t_{lag}$, is derived from the DoB plot. The desirable characteristics of such a second liquid meal are at least one of the effects of 1) to cause a distension effect in the proximal stomach, or 2) to have a high caloric value or low pH value, so that inhibition of gastric emptying is required. Therefore, one preferred and desired approach is to administer the same liquid test meal as was administered in the first meal but with a large amount of water, so as to induce stress of the fundus, and thus to measure the emptying rate of meals of similar caloric content but with different volumes. According to different preferred embodiments, this second meal can be either with or without an isotope labeled substrate. If no isotope labeled substrate is used, the effect of gastric accommodation of the first meal is determined by means of the effect on the first emptying curve, if present. In this case, it is important that the second meal be a low natural $^{13}C$ source, so that it does not interfere with the $^{13}CO_2$ levels generated from the metabolized $^{13}C$-labeled substrate used in the first meal.

Figure 3:
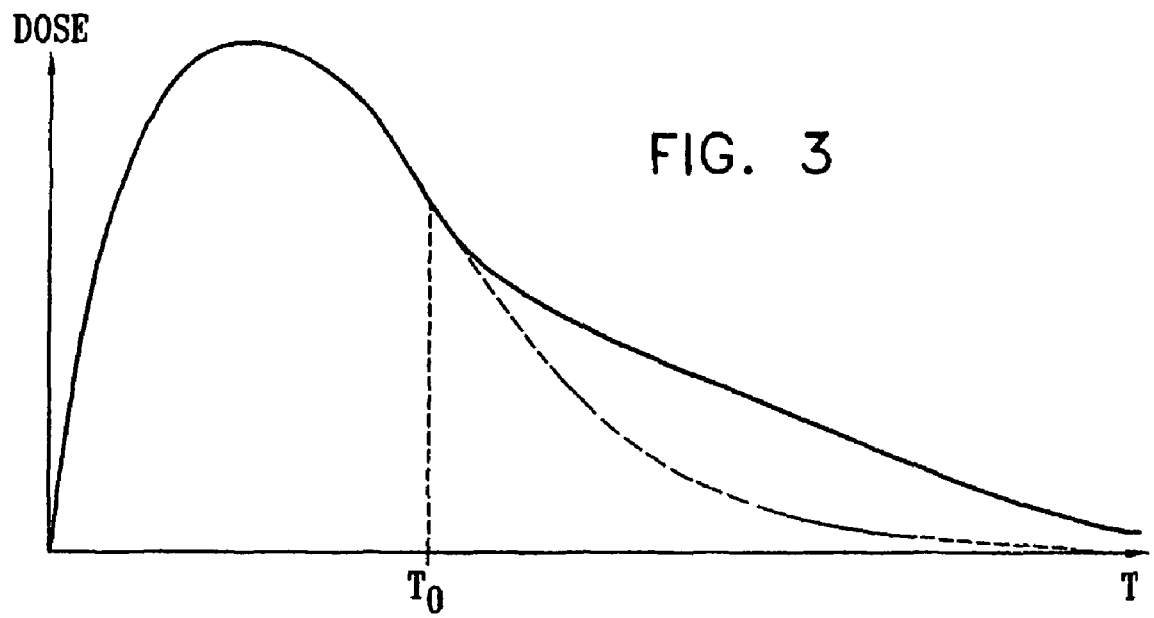
FIG. 3 is a schematic drawing of a curve of the DoB or of the exhaled dose of labeled decomposition product obtained in a GEBT performed with an unlabelled second meal.

This effect is shown by reference to FIG. 3, which is a schematic drawing of a curve of the DoB or of the exhaled dose of labeled decomposition product obtained in a GEBT performed with an unlabelled second meal. At the time $T_0$, at which time the gastric emptying parameters have been determined with sufficient accuracy, the second meal is administrated. The extrapolated shape of the curve beyond time $T_0$, which would have been obtained without the administration of the second meal, is shown as a dotted line. The values of gastric emptying parameters obtained from this curve are recorded as soon as available, i.e. after time $T_0$. Administration of the second meal may result in a change in the asymptotic tail end of the curve, as shown by the solid line. New values of gastric emptying parameters are now calculated for this new curve, and the values compared with the gastric emptying parameters originally obtained from the initially obtained curve. In a normal subject, the values of gastric emptying parameters will be little changed, if at all, while a subject with impaired gastric accommodation will generally show noticeably changed values.

In the case of an isotopically labeled second meal, the preferred procedure is simpler and more direct, since a new curve can be modeled directly for the second meal and a new set of gastric emptying parameters is calculated to determine the emptying rate of the second meal directly, as explained hereinbelow. The effects of the second meal on the emptying curve depend upon the composition of the meal. In a normal subject, the second liquid meal does not generally significantly affect the shape of the second emptying curve, which has a normal shape, similar to that of the first meal, as shown by the similarity of the two curves shown in FIG. 4. The first meal shown in FIG. 4 was of 200 ml. of Ensure Plus, with 50 mg. of $^{13}C$-sodium acetate added thereto. The second meal was 200 ml. of Ensure Plus with 600 ml of additional water, and 100 mg. of 13C-sodium acetate added thereto.

Figure 5:
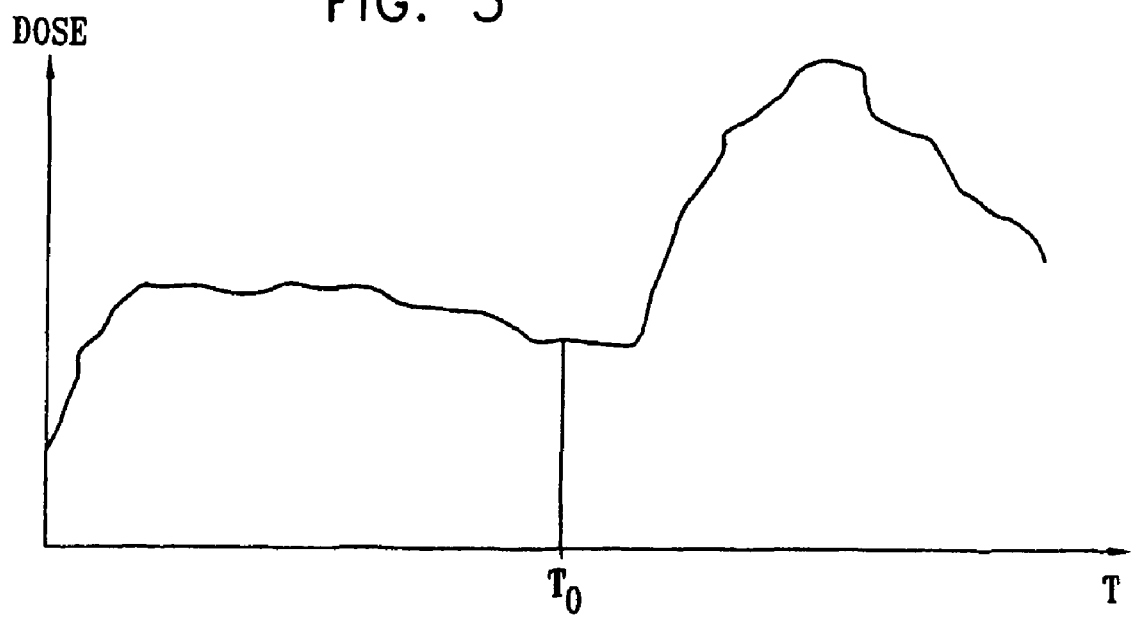
FIG. 5 is a typical DoB curve as a function of time, resulting from the two meal procedure for a subject with a gastric accommodation disorder.

On the other hand, in subjects with some forms of gastric accommodation disorder, a possible outcome of the breath test conducted according to this preferred embodiment, would be to change the shape of the emptying curve on administration of the second meal, as typically shown in FIG. 5. In the example brought in FIG. 5, using the same meals as those used in the test illustrated in FIG. 4, it is observed that the gastric emptying is significantly quicker for the second meal than for the first. For the subject tested in FIG. 5, for instance, $t_{1/2}$ was found to be 174 minutes for the first meal (200 ml) and only 112 minutes for the second, high volume meal (800 ml), thus showing that the subject has a significant gastric accommodation anomaly.

It is to be understood that the gastric emptying and gastric accommodation breath tests described in the above-mentioned preferred embodiments may be performed by any suitable breath test apparatus, whether using an on-line, real time gas analyzer, or whether the subject's exhaled breaths are collected in individual bags and are then transferred to a remote gas analysis instrument, such as a mass spectrometer. Furthermore, those of the methods which are amenable thereto, can also be performed using scintigraphy, CT, MRI, ultrasound, or any other means known in the prior art for investigating and determining gastric functioning.

However, if breath tests, according to these preferred embodiments, are performed using an on-line, real-time breath test analyzer, such as the BreathID apparatus supplied by Oridion Medical Ltd., or as described in the above mentioned U.S. patent documents, then the second meal can be administered to the subject at the earliest possible time, either before the peak or after the peak, according to the requirements of the test and the response of the subject. Use of such apparatus thus shortens the test in comparison with the other possible ways of applying the preferred methods of the present invention According to one preferred procedure for applying this first method, after measurement of the baseline isotopic level, the subject is given 75 mg of $^{13}C$-sodium acetate dissolved in 200 ml of a standard high caloric liquid test meal, such as Ensure Plus, or similarly available alternatives. Alternatively and preferably, the $^{13}C$-sodium acetate can be pre-dissolved in 5 ml-15 ml of water to facilitate its incorporation into the caloric liquid meal. After meal administration, breath samples are collected and analyzed by the breath analyzer at frequent intervals, or even quasi-continuously, and their DoB measured in real time, as described in the prior art. The resultant curve is fitted and extrapolated from the measured points, as previously explained, and the gastric emptying rate parameters are computed in real time, as well as their convergence towards their asymptotic values. A possible method to calculate the convergence of the gastric emptying parameters is to plot them as a function of time and to compute the derivative of the last measurement points, using the computing system that controls the breath analyzer, as described in the above-referenced U.S. patent documents. When the derivatives approximate to zero the convergence of the parameters is achieved. The above mentioned point in time $T_0$ at which the second test meal is administered, is assumed to be reached as soon as the convergence of $t_{1/2}$ and $t_{lag}$ is decided as definitely known, so that their values can be compared with those of the emptying curve of the second meal.

Figure 6:
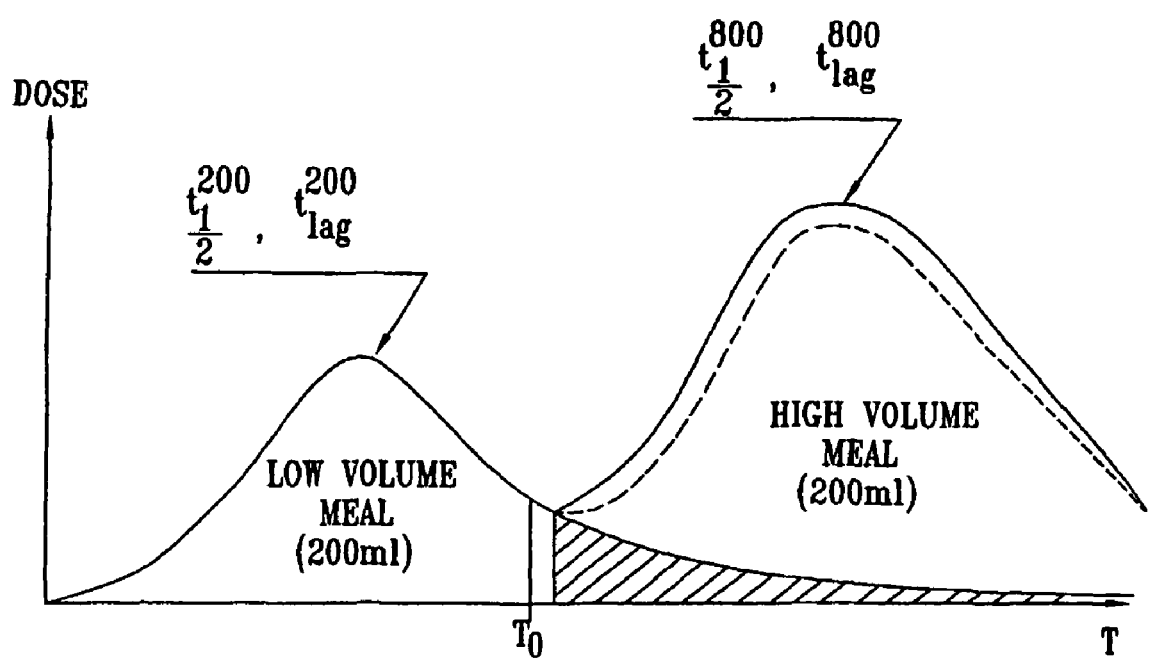
FIG. 6 illustrates schematically how compensation is made in the second meal curve for residual parts of the first meal still residing in the gastrointestinal tract, with isotopic $^{13}C$-cleavage products that have not been exhaled by the lungs yet.

According to the preferred embodiment wherein the second meal is also labeled, the second meal also preferably comprises 75 mg of $^{13}C$-sodium acetate dissolved in 200 ml of a standard high caloric liquid meal, but diluted with an additional 600 ml of water. The $t_{1/2}$ and $t_{lag}$ parameters are now calculated for the second test meal from the time $T_0$ when it is administered. However, at least during the first period after administration of the second meal, a residual part of the first meal still resides in the gastrointestinal tract, with its isotopic $^{13}C$-cleavage products that have not been exhaled by the lungs yet. These residuals from the first meal would therefore interfere with the results obtained from the isotopically labeled second meal. Reference is made to FIG. 6, which illustrates schematically how this physiological interference is compensated for. As it is shown in FIG. 6, after computing the shape of the first curve, and extracting from it values of the $t_{1/2}$ and $t_{lag}$ parameters for the low volume meal, the curve is extrapolated beyond the time To at which the second meal is administered, and the residual values of the extrapolated curve are subtracted from the measurement points to generate a corrected measurement curve from which the values of the $t_{1/2}$ and $t_{lag}$ parameters for the high volume meal are obtained. The actual measured curve is shown by the full line in FIG. 6, and the corrected curve by the dotted line.

The deviation between the set of parameters of the first meal and of the second meal is calculated. In individuals with a gastric accommodation disorder, the rate of emptying of the high volume second liquid meal is faster than for the first liquid meal. It is an indication of increased intra-gastric pressure, and therefore an indication of an accommodation problem. In a number of analyses performed, the emptying half-time of symptomatic patients was found to be at least 20% faster for the second meal. In addition, in these same test, a significant decrease in $T_{lag}$ (lag time) was observed in subjects with impaired accommodation. It is to be understood that these results are results obtained in tests performed using this preferred method of the present invention, and it is not clear that they will be substantiated in full scale clinical studies. They are brought only to illustrate the use of this novel preferred method, and are not intended to limit the method in any way, nor is the performance of the method dependent on the outcome of these results.

Reference is now made to FIG. 7, which is a table showing the deviation of the gastric emptying parameters between a series of subjects, some showing abnormal gastric accommodation and some being asymptomatic. Results for the first method described hereinabove are shown on the left hand half of the table, labeled "Two meal procedure". These results are also compared with those obtained from an alternative preferred method, called the "Two test procedure", to be described hereinbelow.

It is seen that the lag phase deviation, expressed by the differences in the $t_{lag}$ parameter, is usually greater in symptomatic subjects. High values of $t_{1/2}$ and $t_{lag}$ in the first meal are also an indication of delayed gastric emptying.

In those embodiments where a high calorie liquid test meal is utilized, in a normal subject, a constant emptying rate is generally found, according to the rate of release of calories for passage to the digestive tract. Especially suitable meals for this purpose are those caloric drinks with a high percent of fats, such as the commercially available Ensure Plus or Nutradrink products. Such a meal forces the stomach to release its caloric content slowly into the small intestine. It also allows the utilization of similar amounts of labeled substrate, independently of the dilution resulting from the different volumes of the test meals.

Figure 8:
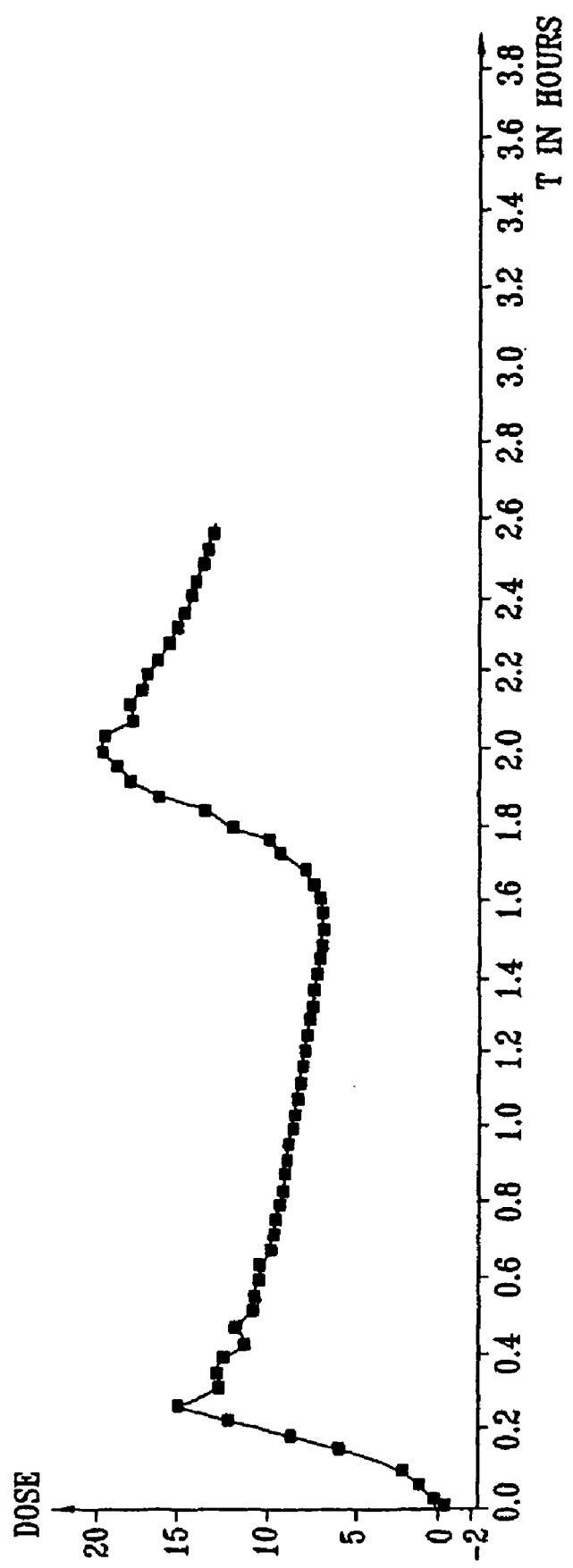
FIG. 8 shows schematic test results of an asymptomatic subject, performing a two-meal test, with a high volume water meal as the second meal.

When only water is utilized as the test meal, using 200 ml and 800 ml of water each with 75 mg. of sodium acetate, for the first and second meal respectively, the above-described tests lose some of their specificity. The test results of an asymptomatic subject, as shown in FIG. 8 indicate that the $t_{1/2}$ time after the high volume water meal was some 25% shorter than that after the low volume water meal, even though the subject was known to be normal, and $t_{lag}$ was unaltered. After performing a similar test with low volume and high volume Ensure Plus test meals, the same subject showed very close values for both $t_{1/2}$ and $t_{lag}$ for the two volumes.

When citric acid is utilized to modulate gastric emptying rate, a significantly slower convergence of the parameters and also a lower specificity is generally found. This is thought to be because the physiological mechanism of the stomach in releasing its contents as a result of the pH of those contents is probably different from the calorific emptying mechanism. Furthermore, pH is affected by dilution, while total calorie count is not. Therefore different test meals amounts must be utilized for the different volumes.

B. The Single Meal Method.

In this preferred embodiment, a single liquid meal with a defined calorie content and containing a labeled marker selected from those described above, is administered to the subject. The size of the liquid meal may preferably be 750 ml. The meal is designed, for instance by means of its low pH or its high calorific value, to ensure that it should remain in the stomach of a normal subject for a certain predetermined time x, such as 60 minutes, and have an emptying rate as defined by the half emptying time, $t_{1/2}$ of y, such as 90 minutes. Upon breath test analysis, a Delta over Baseline curve is traced and the curve of the liquid emptying though the stomach is determined from the outcome. The gastric emptying parameters are determined from this curve.

In subjects having a rate of emptying of the liquid meal faster than normal, this may be an indication of increased gastric pressure, and therefore an indication of an accommodation problem. A possible outcome of the breath test would be a change in the slope of the emptying curve.

Figure 9A:
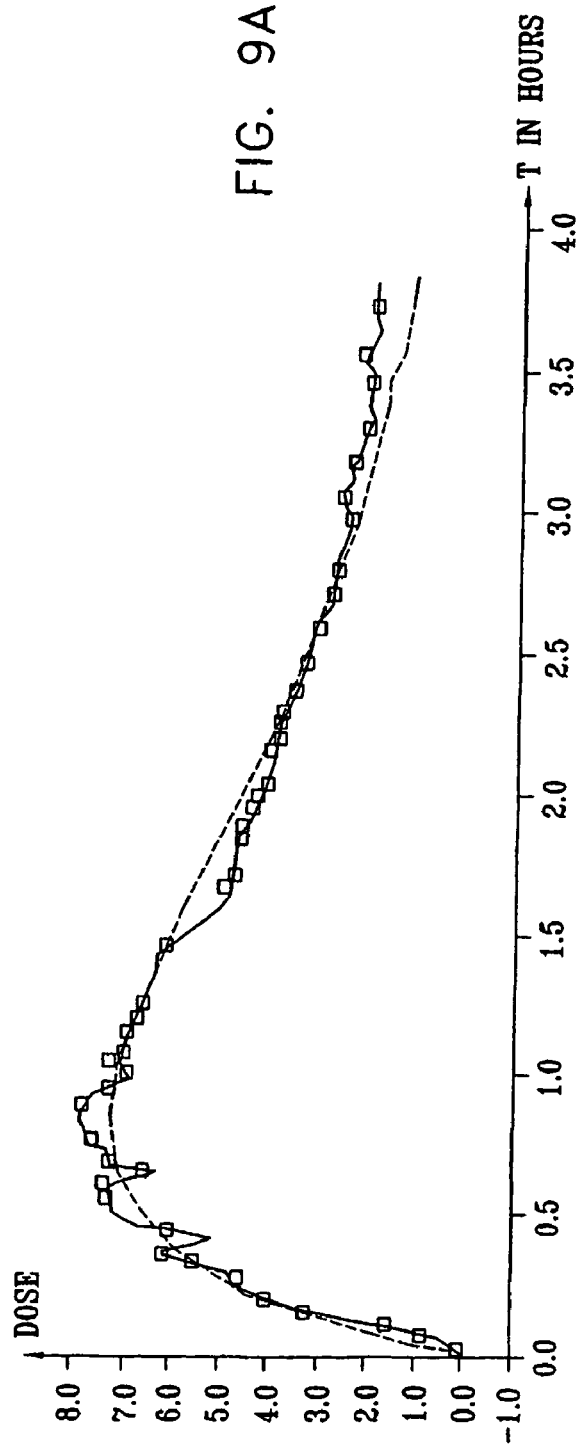
FIGS. 9A and 9B show schematic samples of gastric emptying curves from normal individuals after administration of low volume and high volume liquid test meals respectively.
Figure 9B:
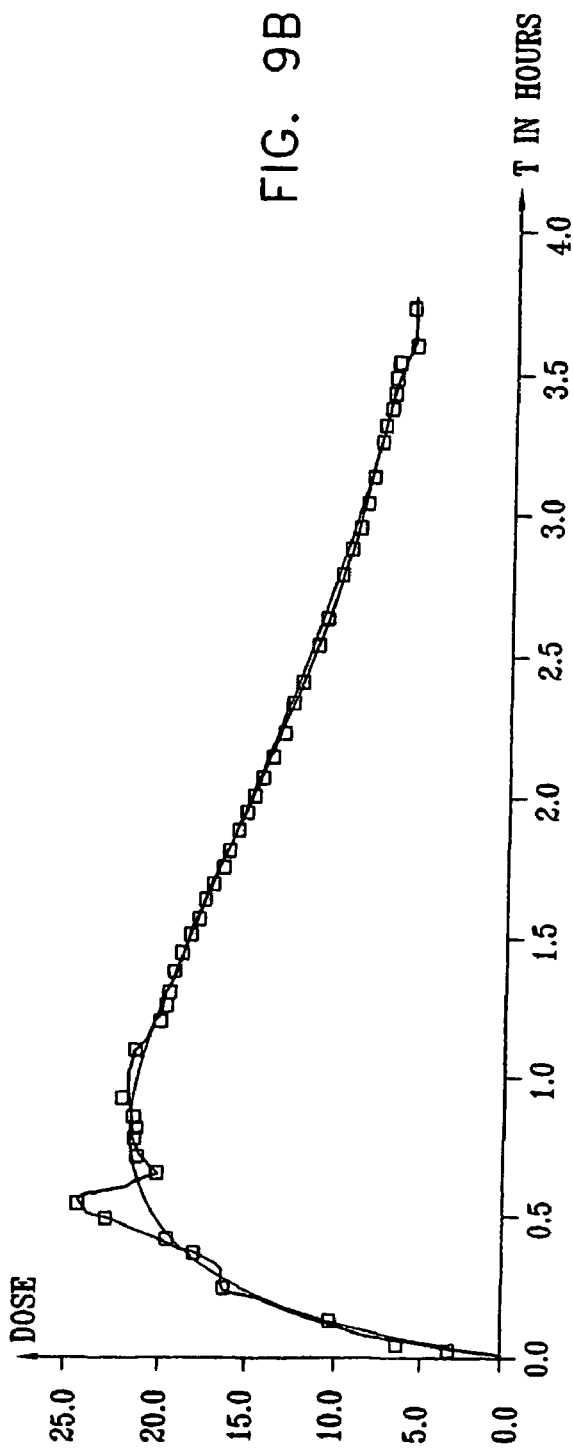

If results are not clear after this first test, the breath test may be repeated using the same meal but in a smaller volume, such as 200 ml, such that the meal is more concentrated. In this way, the effect of volume alone can be compared, as explained in the two test method hereinabove. Samples of curves from normal individuals after administration of low volume and high volume liquid test meals are shown in FIGS. 9A and 9B respectively.

The disadvantage of the single meal method is that there can be some reduction in sensitivity in subjects who suffer from delayed gastric emptying together with impaired gastric accommodation.

C. The Two Test Procedure.

In this preferred embodiment of the methods of the present invention, the tests are essentially the same as those described in the two meal method described above, but are preferably performed on two different occasions, at times sufficiently spaced apart that the effects of the first meal, including effects right down the metabolic pathway of the labeled substrate, have essentially dissipated before the second meal is administered. Typically, the two test method is performed on two successive days, but where it is possible or desirable, a first test early in the morning followed by the second test later in the day is also an operable option. On each of these two separate occasions, a test meal is administered with an identically labeled substrate, but with a different volume. The parameters of the normal ranges of gastric emptying and the test curves are determined and the relative deviation between the parameters of the curves for each measurement with its specific test meal volume are calculated. This approach may provide greater confidence than using one test, with one type of meal alone.

According to one preferred embodiment of the two-test procedure, the tests are performed on the subject on two different days. On the first day, after a baseline isotopic breath measurement is taken, the subject is administered 75 mg of $^{13}$C-sodium acetate dissolved in 200 ml of a standard high caloric liquid test meal, such as Ensure plus. Alternatively the $^{13}$C-sodium acetate can be initially dissolved into 5 ml-1 5 ml of water to facilitate its incorporation into the caloric liquid meal. After the meal administration, breath samples are repeatedly or continuously collected by a breath analyzer and their DoB measured in real time, as is known in the art. The measurement curve is fitted to the results of the analyses, the gastric emptying rate parameters are computed therefrom in real time, and their asymptotic convergence values determined. On the second day, the same procedure is repeated, but the meal is amended by the addition of 600 ml of water to the 200 ml of standard high caloric liquid test meal with 75 mg of $^{13}$C-sodium. The gastric emptying rate parameters are again calculated for this second meal, and their deviation from those of the first meal calculated. Some typical test results for a symptomatic subject are shown in FIGS. 10A and 10B. In FIG. 10A, a 200 ml. high caloric test meal is administered on the next day to the same subject, and the value of $t_{1/2}$ is found to be 156 minutes. In FIG. 10B, an 800 ml. high caloric test meal is administered, and the value of $t_{1/2}$ is found to be 99 minutes.

The above three described procedures have been described in terms of their implementation in the form of breath tests. However, it is to be understood that the concepts underlying the above-described methods for the measurement of gastric emptying parameters could also be performed by using different measurement methods other than those of breath testing. Such methods include, but are not meant to be limited to, the use of radioactive isotope tracking using $^{99}$Te, $^{14}$C or other labeled substrates, the use of ferromagnetic materials as markers to be tracked, the use of contrast materials in X-ray or CT methods, or the use of gas bubbles in ultrasound imaging, and alternative measurement methods using such techniques as magnetic resonance, gamma imaging or scintigraphy. Each of these methods, as known in their respective arts, and including those described according to the present invention, is characterized by its own sensitivity, specificity and convenience according to the meal utilized, population, clinical setting or the measurement equipment utilized.

New mathematical methods to determine gastric emptying rate have been currently proposed as alternatives to those already described in "$^{13}$C-Breath Test Modeling" by Tom Preston, East Kilbride. Department of Child Health and School of Veterinary Science, University of Glasgow. These methods are based on coupling different differential equations, or their equivalent, normalized to the Heaviside function, to each different metabolic or physiologic process. Thus different parameters are obtained for each equation and are combined to obtain $t_{1/2}$ and $t_{lag}$ or their equivalents. These calculation methods differ from those known in the art only in their mathematical approach, and are based on the same breath test procedures or gastric emptying studies as those used in the scintigraphic analysis.

It has been observed in gastric accommodation procedures that the amount of labeled substrate does not affect parameters such as $t_{1/2}$ and $t_{lag}$, but only those related to the isotopic amplitude, such as the GEC, which shows mathematical homogeneity. It is therefore to be understood that the preferred methods of the present invention are not meant to be limited to any specific method of calculation of the gastric emptying rate parameters, but are applicable to alternative mathematical models also, such as that described above.

According to further preferred embodiments of the present invention, it is also proposed that it is of clinical significance to differentiate between either mechanical or chemical causes of the impaired gastric accommodation. It is an objective of the present invention to provide this indication by means of recording the symptomatic response of the tested subject to the meals when the test is performed. Thus, in the Two Meal Procedure and Two Test Procedure methods for investigating patients with suspected defective gastric accommodation, if, discomfort symptoms are observed only when a high volume test meal is administered, then the symptoms are an indication of a mechanical response to the volume. When discomfort symptoms are recorded with the small meal, it is an indication of symptoms related to caloric composition or acidic composition of the meal, or what is termed "chemical stress sensations". There exist several methods to measure discomfort symptoms, such as symptom questionnaires, clinical observation, facial recognition, biofeedback, as is well known in the clinical arts.

4. Bacterial Overgrowth Breath Test (BOBT)

Other known causes of dyspepsia, IBS or gastrointestinal illness are bacterial overgrowth, or the colonization of the small intestine or the upper gastrointestinal tract by colonic bacteria, lactose intolerance, malabsorptions of other sugars, or low gastrointestinal motility. With respect to bacterial overgrowth, the assessment of the level of these microorganisms outside the large intestine is usually performed either by means of gastroscopy, which is cumbersome, patient uncomfortable and depends on human interpretation, or by means of a hydrogen breath test (HBT). The HBT is performed by analysis of the breath before and after administering to a subject of a quantity of a marker sugar, such as lactulose, which is not broken down in the stomach. Bacteria break down the lactulose to produce hydrogen, a gas not produced by large organisms such as humans, as a natural result of the lactulose metabolism. Thus an increase in hydrogen level measured in the breath of a subject is an indication of bacterial activity. The time taken for the lactulose to reach the large intestine, as for other sugars which are not broken down in the stomach, is around 3 hours. Therefore an earlier hydrogen peak is a signal of bacterial overgrowth.

The main disadvantage of this prior art HBT is the need to identify the exact time during which the meal is passing through the small intestine. Because of variation in gastrointestinal transit times, both between different subjects and even in the same subject at different times, false negative and false positive diagnoses may arise.

Therefore to overcome these drawbacks a breath test is proposed, according to yet another preferred embodiment of the present invention, in which a substrate is administered, containing not only a substance such as lactulose which generates hydrogen in the presence of bacteria, but also containing a second isotopically labeled marker which is operative to indicate the location of the substrate within the intestinal tract. The hydrogen production is measured to indicate the fermentation action of bacterial flora, if any, and a second measurement of the decomposition products of the second marker is typically made at the same time as the measurement of the hydrogen output. The second measurement may preferably be the measurement of labeled $CO_2$ produced as the result of metabolism by the subject of a labeled carbon substrate.

According to a preferred embodiment of the present invention, a $H_2$ detector such as an electrochemical spirometer or a gas chromatographer is incorporated in an isotopic gas analyzer being part of a breath test apparatus. Preferably, sample gases are collected in a control range of $CO_2$ concentrations by means of an intermediate cell, as described in the prior art.

Several different types of substrate may preferably be used to check both $H_2$ production in the small or large intestine, and the passage of the substrate through the intestines. According to a first preferred method of performing this breath test, a relatively large amount of glucose or lactulose, such as 100 g, are administered to the subject, together with a relatively small amount of $^{13}$C-labeled substrate that is rapidly absorbed or metabolized by the body in the intestine such as 100 mg of glucose or sodium acetate or microencapsulated bicarbonate, for measurement of labeled $CO_2$ production. The glucose is absorbed and rapidly metabolized by the patient's body only when it reaches the small intestine, at which point it can be detected as labeled $CO_2$ in the subject's breath. The glucose can also be metabolized by bacteria, which is detected as $H_2$ in the breath. If the gaseous peaks of $^{13}CO_2$ and $H_2$ are correctly separated in time, in that the $^{13}CO_2$ peak occurs at least a predetermined time before the $H_2$, this indicates that the location of the subject's bacterial population is normal. This situation is illustrated in the schematic breath test results shown in FIG. 11. If, on the other hand, the $H_2$ peaks at a time close to the $^{13}CO_2$ peak, it indicates the presence of bacterial overgrowth in the small intestine, as shown schematically in FIG. 12. It should be noted that the "peak" of the hydrogen exhalation if far broader and long lasting than that of the $^{13}CO_2$ peak, and references to the $H_2$ peak as such, and its temporal position relative to the $^{13}CO_2$ peak, and as claimed, are to be thus qualified. Indeed, in most practical cases, instead of measurement of the "peak" position of the hydrogen, a measurement of $H_2$ exhalation is determined by the position at which the hydrogen exhalation achieves a certain level above the baseline level.

In a normal individual, the glucose is absorbed and metabolized by the body in the small intestine. Any remaining glucose will be available in the large intestine to provide a detectable hydrogen peak upon bacterial metabolism. In some instances, however, not enough glucose will remain to be passed to the large intestine to provide a detectable hydrogen peak from bacterial metabolism in a normal subject. In this case, a non-breakdownable sugar such as lactulose is included as a test substrate.

Figure 13:
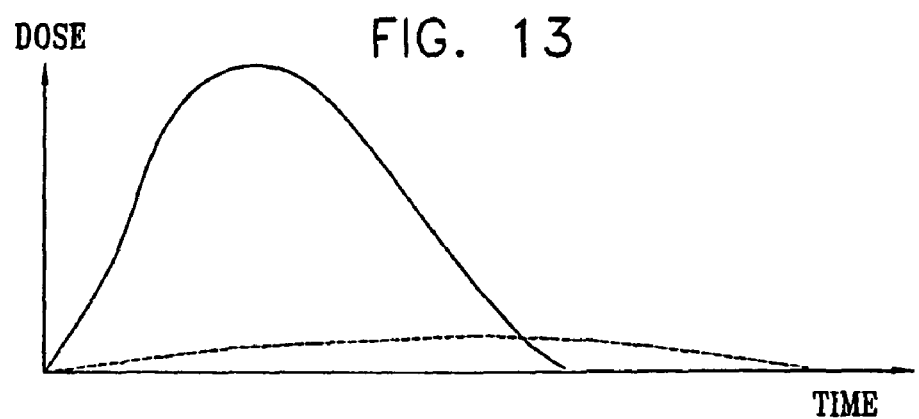

In another example, 100 mg of a $^{13}C$ labeled substrate is administered together with a dedicated test substrate for a bacterial overgrowth hydrogen breath test, such as 10 grams of lactulose. As mentioned above, if the $^{13}CO_2$ peaks significantly before the $H_2$ this indicates that the location of the patient's bacterial population is normal, as shown schematically in FIG. 11. If the $H_2$ "peaks" at around the same time as the $^{13}CO_2$ peak, it indicates the presence of bacterial overgrowth in the small intestine, as shown schematically in FIG. 13. In this example, however, the presence of a non-breakdownable sugar such as lactulose as a test substrate ensures that a hydrogen peak will be detected, whether in the small intestine in a subject with bacterial overgrowth, or in the large intestine of a normal subject. $^{13}CO_2$, originating from the known metabolism of the $^{13}C$-labeled substrate, is a marker peak to determine the point which the meal has reached in the gastrointestinal tract, and therefore, overcomes differences in digestion speed due to different metabolic dynamics, or due to the clinical state of the subject. This preferred method therefore overcomes the prior art disadvantage of intra-and inter-patient variation in gastrointestinal transit times.

According to further preferred embodiments of the present invention, the joint use of a hydrogen and a $CO_2$ marker in the ingested substrate also provides a method to determinate accelerated or delayed orocecal transit time. This is the time between the oral administration of the food and its arrival at the colon, where the colonic bacteria ferment the sugars. This process could be characterized by a high peak of hydrogen with a low labeled $CO_2$ production.

Other alternatives tests meals include, but are not limited to, labeled sodium acetate, sodium octanoate, glucose, a probe such as acetyl leucine, or a microencapsulated labeled substrate, together with a relatively large amount such as 70-100 g of unlabeled glucose, or 10 g of lactulose.

According to yet further preferred embodiments of the methods of the present invention, these substrates, provided in large amount, could be incorporated into a microencapsulation means, designed to allow their release only in the alkaline intra-intestinal media. This enables an improvement to be achieved in the accuracy in time of the test. Alternatively, the two components can be provided separately in the same meal, this being a particularly simple method of application. Single labeled substrates and dual/single microencapsulated markers have the advantages over the prior art that the absorption and metabolization by the body and/or bacterial fermentation are produced simultaneously at the GI tract.

Alternatively and preferably a microencapsulated formulation, which is breakdownable at the colon, containing a labeled substrate of rapid release as bicarbonate could be utilized to show orocecal gastric time.

Figure 12:
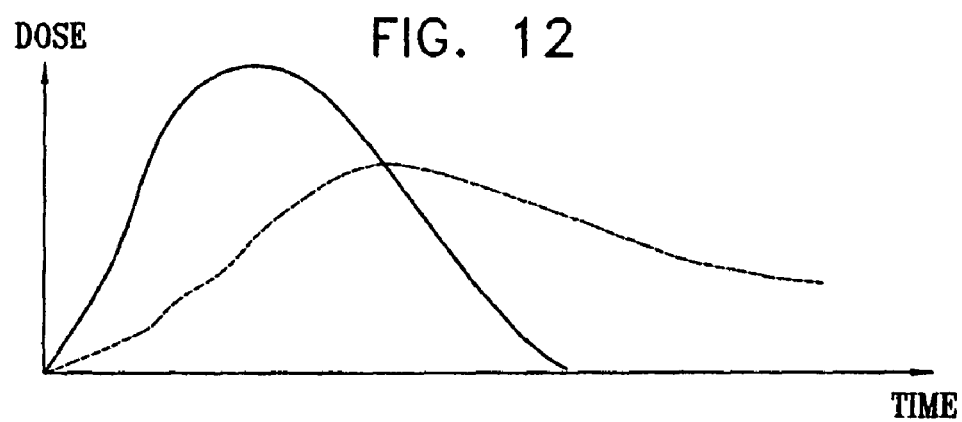

According to another preferred embodiment of the present invention, there is provided a method to improve the accuracy of and to shorten the duration of the lactose breath test (LBT), as well other sugar malabsorption breath tests, such as fructose or maltose or sucrose intolerance. It is believed that lactose intolerance occurs in 25% of the general population and is characterized by the low availability in the body of lactase, the enzyme which metabolizes the lactose in milk into glucose and galactose, for utilization by the body. As a consequence of this lactase deficiency, the unmetabolized lactose is fermented by colonic bacteria, producing detectable $H_2$. Simultaneous measurement of $^{13}CO_2$ and $H_2$ after $^{13}C$-lactose ingestion has been proposed for diagnosing lactose-intolerance, to detect such absorption of the unmetabolized lactose in the colon. Unfortunately, $^{13}C$-labeled lactose is expensive and not easily available, making this an unattractive method of testing. The production of naturally $^{13}C$-labeled lactose has been suggested, by feeding milk-producing cows with $^{13}C$-enriched feed, which is reasonably cheaply available. However, the enrichment levels of such milk are too low to produce acceptable results and their variability is too high for standardization. There is thus provided, according to another preferred embodiment of the present invention, a method of providing a dual meal for detecting lactose intolerance. The dual meal comprises natural lactose, together with a labeled marker substrate, such as $^{13}C$-labeled xylose, a sugar which is mainly absorbed only when it gets to the colon, and which is readily available at low cost. Thus after ingestion of the dual meal, if the $^{13}CO_2$ is detected approximately at the same time as $H_2$, as shown in FIG. 12, it is a sign that the lactose has not been absorbed in the small intestine, due to the absence of lactase enzyme, but has reached the colon together with the labeled lactulose. If on the other hand, no $H_2$ is detected with the $^{13}CO_2$, this is a sign that the lactose has been correctly absorbed in the small intestine, and that the subject does not suffer from lactose intolerance. Additionally, the use of this meal enables the test time to be shortened, since it is known that the $H_2$ peak is expected shortly after the $^{13}CO_2$ peak if there is a deficiency of endogenous lactase, such that there is no need to wait an extended time to see whether an $H_2$ peak appears or not.

Figure 11:
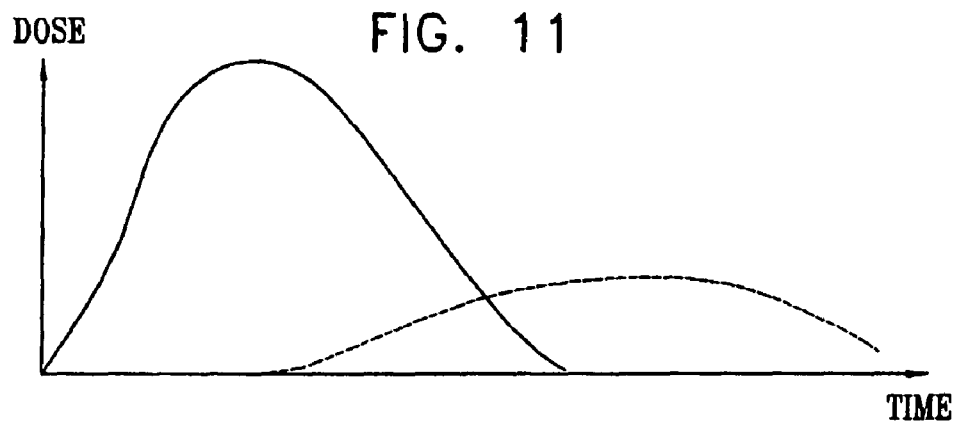
FIGS. 11 to 13 are schematic examples of curves obtained, each showing both a hydrogen peak and an isotopically labeled carbon dioxide peak, to illustrate the results obtained from subjects with different IBS disorders, including bacterial overgrowth and sugar malabsorbtions.

According to yet another preferred embodiment of the present invention, a dual meal comprising lactose and a marker substrate absorbed in the small intestine, such as $^{13}C$-labeled sodium acetate, could be used to determine the presence of either sugar malabsorption, such as lactose intolerance or of bacterial overgrowth or of both. If the subject suffers from bacterial overgrowth but not from lactose intolerance, most of the lactose is rapidly absorbed in the small intestine, but a small quantity generates hydrogen because of contact with the bacterial overgrowth there. As a consequence, a small $H_2$ peak occurs approximately at the same time as the $^{13}CO_2$ peak as the meal is passing through the small intestine, as shown in FIG. 11. If on the other hand, the subject has lactose intolerance, then a large $H_2$ peak occurs when essentially all of the lactose reaches the bacteria in the colon, and this occurs later than the $^{13}CO_2$ peak, produced during passage of the labeled sodium acetate through the small intestine, as previously explained. If the subject suffers from both disorders, then the absence of a lactose absorption mechanism results in all of the lactose being available in the small intestine for exposure to the bacterial overgrowth therein, and the result is a large $H_2$ peak occurring at the same time as the $^{13}CO_2$ peak.

Alternatively a labeled substrate that is metabolized at the colon such as xylose or microencapsulated bicarbonate could be utilized together with the lactose. In such a case, an early hydrogen peak and a later peak of the labeled substrate is a sign of bacterial overgrowth. The two peaks concurrently is a sign of lactose intolerance.

According to yet another preferred embodiment of the present invention, $^{13}C$-labeled glucose, sodium acetate or another $^{13}C$-labeled material, could be utilized in a solid/liquid test meal including glucose or lactulose for the combined assessment of gastric accommodation, gastric emptying and bacterial overgrowth in one test at the same opportunity, thereby reducing the number of visits which the patient has to make to the clinic.

The bacterial overgrowth breath test can be summarized by the following points:
1. A meal is labeled with a $^{13}C$ labeled material that is absorbed in the small intestine and produces a $CO_2$ peak as soon as the meal passes through the small intestine
2. The same meal produces an $H_2$ peak in a Breath Test (BT) when it gets to normal bacterial concentrations in the large intestines.
3. The use of a non-broken down sugar, such as lactulose, as used in prior art, determines bacterial overgrowth according to the time taken for the $H_2$ peak to develop.
4. Perform the BT to detect both $CO_2$ and $H_2$ peaks. If the peaks are correctly separated in time, the patient's bacterial location is normal. If the $H_2$ peaks at a time close to the $CO_2$ peak, it indicates the presence of bacterial overgrowth in the small intestine.
5. The advantage is that with $CO_2$ as a marker peak to determine where the meal has got to in the GI tract, differences in digestion speed due to different metabolisms, or to the clinical state of the patient are overcome.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of determining at least a first and a second gastro-intestinal condition in a subject, the method comprising:
    administering to said subject a test meal comprising a labeled marker whose by-products are absorbed and exhaled in breaths of said subject after exit from the stomach of said subject;
    performing on said subject a breath test indicative of at least one of the first and the second gastro-intestinal conditions; and
    automatically determining the first and the second gastro-intestinal conditions in said subject based on the same meal.

2. A method according to claim 1 and wherein at least one of said first and said second gastro-intestinal conditions comprises at least one of dyspepsia and irritable bowel syndrome.

3. A method according to claim 1 and wherein at least one of said first and said second gastro-intestinal conditions comprises at least one of a gastric emptying disorder, a gastric accommodation disorder, and a *Helicobacterpylori* infection.

4. A method according to claim 1 and wherein at least one of said first and said second gastro-intestinal conditions comprises at least one of a sugar malabsorption disorder, a bacterial overgrowth, a gastric emptying disorder, and an orececal transit time disorder.

5. A method according to claim 4 and wherein said sugar malabsorption disorder is at least one of lactose intolerance, fructose, intolerance, sucroseintolerance and maltose intolerance.

6. A method according to claim 1, wherein a type of the breath test indicative of the second gastro-intestinal condition is selected based on a result of the breath test indicative of the first gastro-intestinal condition.

7. A method according to claim 1, wherein said first gastro-intestinal condition comprises a gastric emptying disorder and said second gastro-intestinal condition comprises a gastric accommodation disorder.

8. A method according to claim 7, wherein said test meal comprises a liquid meal having a predetermined volume, at least one average gastric emptying characteristic of said meal for a large plurality of normal subjects being known,
    wherein determining said first gastro-intestinal conditions comprises determining at least one emptying characteristic of said meal from the stomach of the subject,
    and wherein determining said second gastro-intestinal conditions comprises determining the gastric accommodation of the subject according to the deviation between said at least one emptying characteristic of said meal from the stomach of said subject and said at least one average emptying characteristic of said meal for a large plurality of normal subjects.

9. A method according to claim 8, and wherein said predetermined volume is sufficient to cause gastric distension in said subject.

10. A method according to claim 8, and wherein said predetermined volume is at least 750 milliliters of liquid.

11. A method according to claim 8, and wherein said liquid meal has a gastric retention characteristic arising from at least one of a predetermined pH, a predetermined calorific value and a predetermined composition of said liquid meal.

12. A method according to claim 11, and wherein said predetermined pH is less than 3.0.

13. A method according to claim 11, and wherein said predetermined calorific value is at least 200 kilocalories.

14. A method according to claim 11, and wherein said predetermined composition is an isotonic composition.

15. A method according to claim 6, wherein said test meal comprises at least two marker materials, a first material which is generally not absorbed in the subject's stomach, and which releases a gas in the presence of bacteria, and a second material operative to indicate location of said meal within the gastro-intestinal tract of the subject; wherein said breath test comprises detection, by means of said first marker material, the generation of said gas in said subject, and wherein said breath test further comprises detection, by means of said second marker material, the position within the subject's gastro-intestinal tract at which said gas is generated.

16. A method according to claim 15, and wherein said gas is hydrogen.

17. A method according to claim 16, and wherein said breath test further comprises detection of a by-product of said second marker material, such that the position of said hydrogen generation in the gastro-intestinal tract of said subject is determined by the temporal relationship between the appearance of hydrogen and of the by-product of said second marker material in said subject's breath.

18. A method according to claim 17, and wherein said second marker material is labeled with a carbon isotope, and said by-product is isotopically labeled carbon dioxide.

19. A method according to claim 16, and wherein said first material is a sugar metabolized in the small intestine of said subject, such that the time of detection of said hydrogen relative to the time of detection of the second marker material is used to determine the presence of bacterial overgrowth in said small intestine.

20. A method according to claim 19, and wherein said second material is a labeled sugar also metabolized in the small intestine of said subject, such that the generally concurrent appearance in the breath of said subject of hydrogen and a by-product of said second marker material is indicative of the presence of bacterial overgrowth in said subject.

21. A method according to claim 19, and wherein said second material is a labeled sugar also metabolized in the small intestine of said subject, such that the appearance in the breath of said subject of a by-product of said second marker material significantly prior to the appearance of hydrogen is generally indicative of the absence of bacterial overgrowth in said subject.

22. A method according to claim 19, and wherein said first material is at least one of glucose and lactulose.

23. A method according to claim 19, and wherein said second material is at least one of labeled sodium acetate, sodium octanoate, glucose, a probe such as acetyl leucine, or a microencapsulated labeled substrate.

24. A method according to claim 16, and wherein said first material is a sugar generally not metabolized in the small intestine of said subject, such that the time of detection of hydrogen relative to the time of detection of said second marker material is used to determine the orocaecal transit time of said subject.

25. A method according to claim 16, and wherein said first material is a sugar of a group thought to be malabsorbed in the small intestine of said subject, such that it arrives essentially unabsorbed at the colon of said subject, where hydrogen is generated by the presence of colonic bacteria, such that the time of detection of hydrogen relative to the time of detection of the second marker material is used to determine a sugar intolerance in said subject.

26. A method according to claim 25, and wherein said second material is an isotopically labeled material generally absorbed in the colon, such that the time of detection of hydrogen relative to the time of detection of said second marker material is used to determine a sugar intolerance in said subject.

27. A method according to claim 26, and wherein said second material is xylose labeled with a carbon isotope, and said by-product is isotopically labeled carbon dioxide.

28. A method according to claim 25, and wherein said second material is an isotopically labeled material generally absorbed in the small intestine, such that the relative time and quantity of detection of hydrogen and labeled by-products of said second marker material is used to determine whether said subject is suffering from one or both of a sugar intolerance and a bacterial overgrowth.

29. A method according to claim 28, and wherein the time of detection of hydrogen, characteristic of a part of said first material in the presence of bacteria, relative to the time of detection of said labeled by-products of said second marker material is used to determine that said subject is suffering a bacterial overgrowth.

30. A method according to claim 28, and wherein the detection of hydrogen later than the detection of said labeled by-products of said second marker material indicates that said subject is suffering from a sugar intolerance.

31. A method according to claim 28, and wherein the time of detection of a first quantity of hydrogen, characteristic of said first material in the presence of bacteria, relative to the time of detection of said labeled by-products of said second marker material is used to determine that said subject is suffering a sugar intolerance and a bacterial overgrowth.

32. A method according to claim 25, and wherein said sugar is at least one of the group consisting of lactose, fructose, maltose and sucrose.

33. A method according to claim 16, and wherein a by-product of said second marker material is also detected by means of a breath test, such that the position of said hydrogen generation in the gastro-intestinal tract of said subject is determined by the temporal relationship between the appearance of hydrogen and of a by-product of said marker material in said subject's breath.

34. A method according to claim 33, and wherein said second marker material is labeled with a carbon isotope, and said by-product is isotopically labeled carbon dioxide.

35. A method according to claim 16, and wherein said first material is a sugar that is not normally phsyiologically metabolized in the small intestine of said subject, such that the time of detection of said hydrogen relative to the time of detection of the second marker material indicating that the test meal is in the small intenstine is used to determine the presence of bacterial vergrowth in said small intestine.

36. A method according to claim 35, and wherein said second material is a labeled sugar also metabolized in the small intestine of said subject, such that the generally concurrent appearance in the breath of said subject of said hydrogen and a by-product of said second marker material is indicative of the presence of bacterial overgrowth in said subject.

37. A method according to claim 35, and wherein said second material is a labeled sugar also metabolized in the small intestine of said subject, such that the appearance in the breath of said subject of a by-product of said second marker material significantly prior to the appearance of hydrogen is generally indicative of the absence of bacterial overgrowth in said subject.

38. A method according to claim 35, and wherein said first material is at least one of glucose and lactulose.

39. A method according to claim 35, and wherein said second material is at least one of labeled sodium acetate, sodium octanoate, glucose, a probe such as acetyl leucine, or a microencapsulated labeled substrate.

40. A method according to claim 16, and wherein said first material is a sugar generally not metabolized in the small intestine of said subject, such that the time of detection of said hydrogen relative to the time of detection of said second marker material is used to determine the orocaecal transit time of said subject.

41. A method according to claim 16, wherein said first material is a sugar of a group thought to be malabsorbed in the small intestine of said subject, such that it arrives essentially unabsorbed at the colon of said subject, where hydrogen is generated by the presence of colonic bacteria, such that the time of detection of hydrogen relative to the time of detection of the second marker material is used to determine a sugar intolerance in said subject.

42. A method according to claim 41, and wherein said second material is an isotopically labeled material generally absorbed in the colon, such that the time of detection of hydrogen relative to the time of detection of said second marker material is used to determine a sugar intolerance in said subject.

43. A method according to claim 42, and wherein said second material is xylose labeled with a carbon isotope, and said by-product is isotopically labeled carbon dioxide.

44. A method according to claim 41, and wherein said second material is an isotopically labeled material generally absorbed in the small intestine, such that the relative time and quantity of detection of hydrogen and labeled by-products of said second marker material is used to determine whether said subject is suffering from one or both of a sugar intolerance and a bacterial overgrowth.

45. A method according to claim 44, and wherein the time of detection of hydrogen, characteristic of a part of said first material in the presence of bacteria, relative to the time of detection of said labeled by-products of said second marker material is used to determine that said subject is suffering a bacterial overgrowth.

46. A method according to claim 44, and wherein the detection of hydrogen later than the detection of said labeled by-products of said second marker material indicates that said subject is suffering from a sugar intolerance.

47. A method according to claim 44, and wherein the time of detection of a first quantity of hydrogen, characteristic of said first material in the presence of bacteria, relative to the time of detection of said labeled by-products of said second marker material is used to determine that said subject is suffering a sugar intolerance and a bacterial overgrowth.

48. A method according to claim 41, and wherein said sugar is at least one of the group consisting of lactose, fructose, maltose and sucrose.

49. A method according to claim 1, wherein said first gastro-intestinal condition comprises a gastric emptying rate and said second gastro-intestinal condition comprises at least one of a gastric accommodation disorder, a sugar malabsorption disorder, a bacterial overgrowth, and orocaecal transit time disorder.

* * * * *